United States Patent [19]
Audia et al.

[11] Patent Number: 5,721,252
[45] Date of Patent: Feb. 24, 1998

[54] 5HT$_{1F}$ AGONISTS FOR THE TREATMENT OF MIGRAINE

[75] Inventors: James E. Audia; Jeffrey S. Nissen, both of Indianapolis, Ind.

[73] Assignee: Eli Lilly and Company, Indianapolis, Ind.

[21] Appl. No.: 642,069

[22] Filed: May 3, 1996

Related U.S. Application Data

[62] Division of Ser. No. 318,329, Oct. 5, 1994, Pat. No. 5,521,196.

[51] Int. Cl.$^6$ .................. A61K 31/445; A61K 31/44
[52] U.S. Cl. .................. 514/323; 514/318; 514/333; 514/339
[58] Field of Search .................. 514/323, 318, 514/333, 339

[56] References Cited

U.S. PATENT DOCUMENTS

| | | |
|---|---|---|
| 3,850,938 | 11/1974 | Derible et al. . |
| 4,359,468 | 11/1982 | Freter et al. . |
| 4,530,932 | 7/1985 | Clemence et al. . |
| 4,710,500 | 12/1987 | Perregaard . |
| 4,742,057 | 5/1988 | Ueda et al. . |
| 4,997,841 | 3/1991 | Oxford et al. . |
| 5,001,135 | 3/1991 | Oxford et al. . |
| 5,017,703 | 5/1991 | Matsuo et al. . |
| 5,036,078 | 7/1991 | Coates . |
| 5,045,550 | 9/1991 | Jaen .................. 514/332 |
| 5,066,660 | 11/1991 | Oxford et al. . |
| 5,118,691 | 6/1992 | Jaen et al. . |
| 5,187,280 | 2/1993 | Jaen et al. . |
| 5,216,001 | 6/1993 | Perregaard et al. . |
| 5,298,520 | 3/1994 | Baker et al. . |
| 5,317,025 | 5/1994 | BruzMagniez .................. 514/323 |
| 5,322,851 | 6/1994 | Perregaard .................. 514/323 |

FOREIGN PATENT DOCUMENTS

| | | |
|---|---|---|
| 378255 | 7/1990 | European Pat. Off. . |
| 438230 | 7/1991 | European Pat. Off. . |
| 91/18897 | 12/1991 | WIPO . |
| 92/13856 | 8/1992 | WIPO . |
| 93/11106 | 6/1993 | WIPO . |
| 94/03446 | 2/1994 | WIPO . |

OTHER PUBLICATIONS

Tacconi et al. "Indole derivatives" CA 63:13193e (1965).
Wyngaarden et al. "Cecil Textbook of Medicine" Sauders Co., (1983) pp. 1940–1942.

*Primary Examiner*—William R. A. Jarvis
*Attorney, Agent, or Firm*—Robert D. Titus

[57] ABSTRACT

This invention provides novel 5-HT$_{1F}$ agonists which are useful for the treatment of migraine and associated disorders.

11 Claims, No Drawings

5HT$_{1F}$ AGONISTS FOR THE TREATMENT OF MIGRAINE

This application is a division of application Ser. No. 08/318,329 filed Oct. 5, 1994 now U.S. Pat. No. 5,521,196.

BACKGROUND OF THE INVENTION

Theories regarding the pathophysiology of migraine have been dominated since 1938 by the work of Graham and Wolff (*Arch. Neurol. Psychiatry*, 39, 737–63 (1938)). They proposed that the cause of migraine headache was vasodilatation of extracranial vessels. This view was supported by knowledge that ergot alkaloids and sumatriptan, a hydrophilic 5-HT$_1$ agonist which does not cross the blood-brain barrier, contract cephalic vascular smooth muscle and are effective in the treatment of migraine. (Humphrey, et al., *Ann. NY Acad. Sci.*, 600, 587–600 (1990)). Recent work by Moskowitz has shown, however, that the occurrence of migraine headaches is independent of changes in vessel diameter (*Cephalalgia*, 12, 5–7, (1992)).

Moskowitz has proposed that currently unknown triggers for pain stimulate trigeminal ganglia which innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers (*Neurology*, 43(suppl. 3), S16–S20 (1993)).

Serotonin (5-HT) exhibits diverse physiological activity mediated by at least four receptor classes, the most heterogeneous of which appears to be 5-HT$_1$. A human gene which expresses a fifth 5-HT$_1$ subtype, named 5-HT$_{1F}$, was isolated by Kao and coworkers (*Proc. Natl. Acad. Sci. USA*, 90, 408–412 (1993)). This 5-HT$_{1F}$ receptor exhibits a pharmacological profile distinct from any serotonergic receptor yet described. The high affinity of sumatriptan at this subtype, K$_i$=23 nM, suggests a role of the 5-HT$_{1F}$ receptor in migraine.

This invention provides novel 5-HT$_{1F}$ agonists which inhibit peptide extravasation due to stimulation of the trigeminal ganglia, and are therefore useful for the treatment of migraine and associated disorders.

SUMMARY OF THE INVENTION

The present invention provides novel optionally substituted 3-<1,2,3,6-tetrahydro-<1-alkyleneheteroaryl>-4-pyridinyl>-1H-indoles and 3-<1-alkyleneheteroaryl>-4-piperidinyl>-1H-indoles of Formula I:

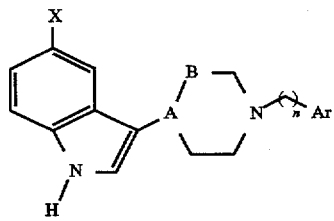

I in which
A—B is —CH—CH$_2$— or —C=CH—;
X is H, halo, C$_1$–C$_4$ alkoxy, C$_1$–C$_4$ alkylthio, C$_1$–C$_4$ alkyl, benzyloxy, hydroxy or carboxamido;
n is 1–4;

Ar is pyridinyl, pyrrolyl or a structure of Formula II:

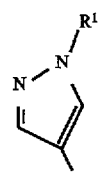

II where R$^1$ is H, C$_1$–C$_6$ alkyl, C$_3$–C$_7$ cycloalkyl, C$_3$–C$_7$ cycloalkylmethyl, benzyl, phenyl or substituted phenyl and pharmaceutically acceptable acid addition salts and hydrates thereof. This invention also provides a pharmaceutical formulation which comprises, in association with a pharmaceutically acceptable carrier, diluent or excipient, a compound of Formula I.

A further embodiment of this invention is a method for increasing activation of the 5-HT$_{1F}$ receptor for treating a variety of disorders which have been linked to decreased neurotransmission of serotonin in mammals. Included among these disorders are depression, migraine pain, bulimia, premenstrual syndrome or late luteal phase syndrome, alcoholism, tobacco abuse, panic disorder, anxiety, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, mutism or trichotillomania. Any of these methods employ a compound of Formula I.

DETAILED DESCRIPTION OF THE INVENTION

The general chemical terms used in the formulae above have their usual meanings. For example, the terms C$_1$–C$_4$ alkyl, C$_1$–C$_4$ alkoxy and C$_1$–C$_4$ alkylthio, include such groups as methyl, ethyl, n-propyl, isopropyl, n-butyl, isobutyl and s-butyl. The term C$_3$–C$_7$ cycloalkyl includes cyclopropyl, cyclobutyl, cyclopentyl, cyclohexyl and cycloheptyl. The term halo includes fluoro, chloro, bromo and iodo.

The term substituted phenyl used in the formula above means a phenyl ring mono- or disubstituted with substituents independently selected from halo, C$_1$–C$_4$ alkyl or C$_1$–C$_4$ alkoxy.

While all of the compounds of this invention are useful as 5-HT$_{1F}$ agonists, certain of the compounds are preferred. It is preferred that n is 2–3 and, when Ar is not a structure of Formula II, it is pyridinyl. It is also preferred that when Ar is a structure of Formula II, R$^1$ is C$_1$–C$_4$ alkyl, phenyl, benzyl, C$_3$–C$_5$ cycloalkyl or C$_3$–C$_5$ cycloalkylmethyl.

It is more preferred that X is H, halo, carboxamido, methoxy or hydroxy and, when Ar is not a structure of Formula II, that it is 3-pyridinyl. It is also more preferred that when Ar is a structure of Formula II, R$^1$ is C$_1$–C$_4$ alkyl, phenyl or C$_3$–C$_5$ cycloalkylmethyl.

It is most preferred that n is 2, X is H, halo or hydroxy and Ar is a structure of Formula II where R$^1$ is C$_1$–C$_4$ alkyl, phenyl or C$_3$–C$_5$ cycloalkylmethyl.

The compounds of this invention are useful in a method for increasing activation of the 5-HT$_{1F}$ receptor for treating a variety of disorders which have been linked to decreased neurotransmission of serotonin in mammals. It is preferred that the mammal to be treated by administration of compounds of this invention is human.

Since the compounds of this invention are amines, they are basic in nature and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluene-sulfonic acid, methanesulfonic acid, oxalic acid, p-bromo-phenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, b-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid or oxalic acid.

The following group is illustrative of compounds contemplated within the scope of this invention:

5-benzyloxy-3-<1-<2-<1-benzyl-1H-pyrazol-4-yl>ethyl>-4-piperidinyl>-1H-indole 5-methoxy-3-<1-<2-<1-hexyl-1H-pyrazol-4-yl>ethyl>-4-piperidinyl>-1H-indole 5-sec-butoxy-3-<1-<3-<1-cyclopentyl-1H-pyrazol-4-yl>propyl>-4-piperidinyl>-1H-indole 5-propoxy-3-<1-<2-<1-ethyl-1H-pyrazol-4-yl>ethyl>-4-piperidinyl>-1H-indole 5-propyl-3-<1-<2-<1-cyclohexylmethyl-1H-pyrazol-4-yl>ethyl>-4-piperidinyl>-1H-indole 5-isopropoxy-3-<1-<2-<1H-pyrazol-4-yl>ethyl>-4-piperidinyl>-1H-indole 5-iodo-3-<1-<4-<1-cyclopentyl-1H-pyrazol-4-yl>butyl>-4-piperidinyl>-1H-indole 5-carboxamido-3-<1-<2-<1-cyclobutylmethyl-1H-pyrazol-4-yl>ethyl>-4-piperidinyl>-1H-indole 5-ethylthio-3-<1-<2-<1-cycloheptylmethyl-1H-pyrazol-4-yl>ethyl>-4-piperidinyl>-1H-indole 5-butoxy-3-<1-<2-<1-(4-isobutylphenyl)-1H-pyrazol-4-yl>ethyl>-4-piperidinyl>-1H-indole 5-bromo-3-<1-<3-<1-(4-ethoxyphenyl)-1H-pyrazol-4-yl>propyl>-4-piperidinyl>-1H-indole 5-chloro-3-<1-<2-<1-(3-propylphenyl)-1H-pyrazol-4-yl>ethyl>-4-piperidinyl>-1H-indole phthalate 5-carboxamido-3-<1-<3-<1-(3-ethylphenyl)-1H-pyrazol-4-yl>propyl>-4-piperidinyl>-1H-indole succinate 5-methoxy-3-<1-<2-<1-(3-isobutoxyphenyl)-1H-pyrazol-4-yl>ethyl>-4-piperidinyl>-1H-indole maleate 5-propoxy-3-<1-<4-<1-(2-methoxyphenyl)-1H-pyrazol-4-yl>butyl>-4-piperidinyl>-1H-indole 5-isopropoxy-3-<1-<2-<1-neopentyl-1H-pyrazol-4-yl>ethyl>-4-piperidinyl>-1H-indole hydrochloride 5-benzyloxy-3-<1-<1,2,3,6-tetrahydro-<2-<1-benzyl-1H-pyrazol-4-yl>ethyl>-4-pyridinyl>-1H-indole 5-methyl-3-<1-<1,2,3,6-tetrahydro-<2-<1-hexyl-1H-pyrazol-4-yl>ethyl>-4-pyridinyl>-1H-indole 5-sec-butoxy-3-<1,2,3,6-tetrahydro-1-<3-<1-cyclopentyl-1H-pyrazol-4-yl>propyl>-4-pyridinyl>-1H-indole p-toluenesulfonate 5-propoxy-3-<1-<1,2,3,6-tetrahydro-1-<2-<1-ethyl-1H-pyrazol-4-yl>ethyl>-4-pyridinyl>-1H-indole 5-hydroxy-3-<1,2,3,6-tetrahydro-1-<2-<1-cyclohexyl-methyl-1H-pyrazol-4-yl>ethyl>-4-pyridinyl>-1H-indole 5-isopropoxy-3-<1,2,3,6-tetrahydro-1-<2-<1H-pyrazol-4-yl>ethyl>-4-pyridinyl>-1H-indole hydrochloride 5-iodo-3-<1,2,3,6-tetrahydro-1-<4-<1-cyclopentyl-1H-pyrazol-4-yl>butyl>-4-pyridinyl>-1H-indole 5-carboxamido-3-<1,2,3,6-tetrahydro-1-<2-<1-cyclobutylmethyl-1H-pyrazol-4-yl>ethyl>-4-pyridinyl>-1H-indole 5-methylthio-3-<1,2,3,6-tetrahydro-1-<2-<1-cycloheptyl-methyl-1H-pyrazol-4-yl>ethyl>-4-pyridinyl>-1H-indole 5-butoxy-3-<1,2,3,6-tetrahydro-1-<2-<1-(4-isobutylphenyl)-1H-pyrazol-4-yl>ethyl>-4-pyridinyl>-1H-indole 5-bromo-3-<1,2,3,6-tetrahydro-1-<3-<1-(4-ethoxyphenyl)-1H-pyrazol-4-yl>propyl>-4-pyridinyl>-1H-indole hydrobromide 5-chloro-3-<1,2,3,6-tetrahydro-1-<2-<1-(3-propylphenyl)-1H-pyrazol-4-yl>ethyl>-4-pyridinyl>-1H-indole phthalate 5-carboxamido-3-<1,2,3,6-tetrahydro-1-<3-<1-(3-ethylphenyl)-1H-pyrazol-4-yl>propyl>-4-pyridinyl>-1H-indole succinate 5-methoxy-3-<1,2,3,6-tetrahydro-1-<2-<1-(isobutoxyphenyl)-1H-pyrazol-4-yl>ethyl>-4-pyridinyl>-1H-indole maleate 5-propoxy-3-<1,2,3,6-tetrahydro-1-<4-<1-(2-methoxyphenyl)-1H-pyrazol-4-yl>butyl>-4-pyridinyl>-1H-indole sulfate 5-isopropoxy-3-<1,2,3,6-tetrahydro-1-<2-<1-neopentyl-1H-pyrazol-4-yl>ethyl>-4-pyridinyl>-1H-indole hydrochloride The compounds of this invention are prepared by methods well known to one of ordinary skill in the art. A majority of the starting indoles are commercially available, however, they may be prepared by the Fischer indole synthesis (Robinson, *The Fischer Indole Synthesis*, Wiley, New York, 1983).

The indoles are condensed with 4-piperidone.HCl.H$_2$O in the presence of a suitable base to give the corresponding 3-(1,2,3,6-tetrahydro-4-pyridinyl)-1H-indoles as illustrated in the following scheme.

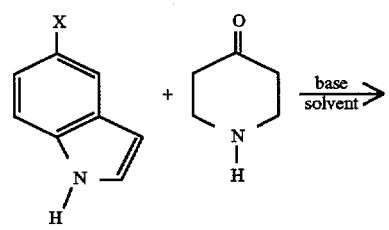

-continued

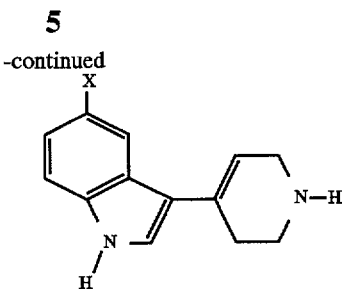

The reaction is performed by first dissolving an excess of the base, typically sodium or potassium hydroxide, in a lower alkanol, typically methanol or ethanol. The indole and two equivalents of 4-piperidone.HCl.H₂O are then added and the reaction refluxed for 8–72 hours. The resulting 3-(1,2,3,6-tetrahydro-4-pyridinyl)-1H-indoles may be isolated from the reaction mixture by the addition of water. Compounds which precipitate may be isolated directly by filtration while others may be extracted with a water immiscible solvent such as ethyl acetate or dichloromethane. The compounds recovered may be used directly in subsequent steps or first purified by silica gel chromatography or recrystallization from a suitable solvent.

The 3-(1,2,5,6-tetrahydro-4-pyridinyl)-1H-indoles may next be hydrogenated to give the corresponding 3-(piperidin-4-yl)-1H-indoles as shown below.

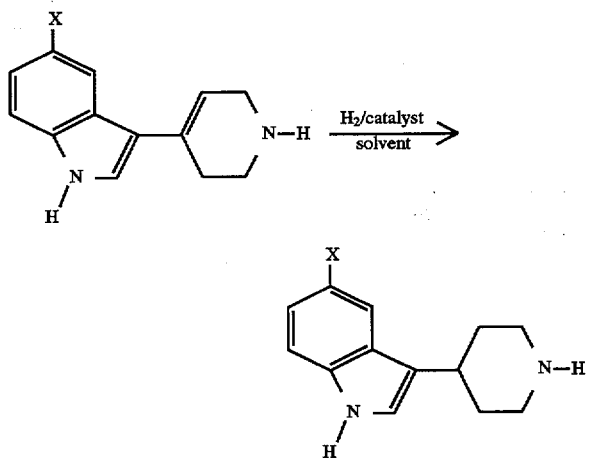

The catalyst may be a precious metal catalyst such as platinum oxide, or palladium or platinum on a suitable support such as carbon. When X is a functional group that is labile to hydrogenolysis, such as halo or benzyloxy, a deactivated catalyst such as sulfided platinum on carbon or a mixed catalyst system of sulfided platinum on carbon with platinum oxide may be used to prevent hydrogenolysis. The solvent may consist of a lower alkanol, such as methanol or ethanol, tetrahydrofuran or a mixed solvent system of tetrahydrofuran and ethyl acetate. The hydrogenation may be performed at an initial hydrogen pressure of 20–80 p.s.i., preferably from 50–60 p.s.i., at 0°–60° C., preferably at ambient temperature to 40° C., for 1 hour to 3 days. Additional charges of hydrogen may be required to drive the reaction to completion depending on the specific substrate. The 3-(piperidin-4-yl)-1H-indoles prepared in this manner are isolated by removal of the catalyst by filtration followed by concentration of the reaction solvent under reduced pressure. The product recovered may be used directly in a subsequent step or further purified by chromatography or recrystallization from a suitable solvent.

Either the 3-(1,2,3,6-tetrahydro-4-pyridinyl)-1H-indoles or the 3-(piperidin-4-yl)-1H-indoles prepared as described above are suitable substrates for N-alkylation with an appropriate alkylating agent as described below.

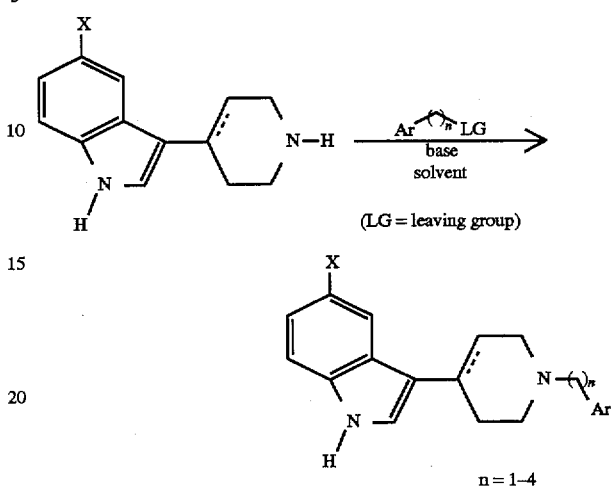

The starting indole and the base are combined in the reaction solvent followed by the addition of the alkylating agent. The reaction solvent may be any non-reactive solvent typically used for alkylations of this type such as acetonitrile, dimethylformamide or N-methyl-2-pyrrolidinone, limited by the solubility of the substrates and a sufficiently high boiling point. The base must be sufficiently basic to neutralize the acid generated during the progress of the reaction but not so basic as to deprotonate other sites in the substrate giving rise to other products. Additionally, the base must not compete to any great extent with the substrate for the alkylating agent and must have sufficient solubility in the reaction solvent. Bases typically used for these reactions are sodium carbonate or potassium carbonate. The reaction mixture is typically stirred at 80° to 140° C., preferably at about 100° C., for 8 hours to 3 days. The alkylated products are isolated by concentration of the reaction mixture under reduced pressure followed by partitioning of the resultant residue between water and a suitable organic solvent such as ethyl acetate, diethyl ether, dichloromethane, ethylene chloride, chloroform or carbon tetrachloride. The isolated product may be purified by chromatography, crystallization from a suitable solvent, salt formation or a combination of these techniques.

The leaving group (LG) of the alkylating agents may be chloro, bromo, iodo, methanesulfonyloxy, trifluoromethanesulfonyloxy, 2,2,2-trifluoroethanesulfonyloxy, benzenesulfonyloxy, p-bromobenzenesulfonyloxy, p-nitrobenzenesulfonyloxy or p-toluenesulfonyloxy, all of which are useful for the preparation of compounds of this invention. The specific alkylating agent employed is determined by its commercial availability or a convenient synthesis from commercially available starting materials. The preferred alkylating agents for synthesis of compounds of this invention are those where the leaving group is chloro or methanesulfonyloxy. Alkylating agents where the leaving group is chloro are prepared from the corresponding alcohol by standard methods, preferably by treating the alcohol with neat thionyl chloride at ambient temperature. Alkylating agents where the leaving group is methanesulfonyloxy are prepared from the corresponding alcohols as described below.

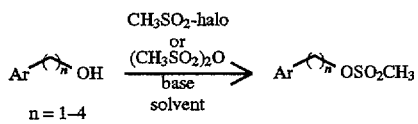

The alcohol is dissolved in a suitable anhydrous solvent such as tetrahydrofuran, diethyl ether, p-dioxane or acetonitrile which contains the base. The base must be sufficiently basic to neutralize the acid generated during the progress of the reaction but not so basic as to deprotonate other sites in the substrate giving rise to other products. Additionally, the base must not compete to any great extent with the substrate for the sulfonating reagent and must have sufficient solubility in the reaction solvent. Bases typically used in these reactions are tertiary amines such as pyridine, triethylamine or N-methylmorpholine. To the reaction mixture is then added the sulfonating reagent with cooling. The sulfonating reagent may be a methanesulfonyl halide such as the fluoride or chloride, or methanesulfonic anhydride. The reaction mixture is allowed to react from 1 hour to 24 hours at ambient temperature. The product is isolated by concentrating the reaction mixture under reduced pressure followed by partitioning the residue between water and an appropriate organic solvent such as dichloromethane, ethylene chloride, chloroform or carbon tetrachloride. The isolated product is used directly in the alkylation step.

The starting alcohols required for the synthesis of compounds of this invention are either commercially available or may be prepared by employing well established synthetic methodology. A general scheme for the synthesis of a number of the required alcohols is described below.

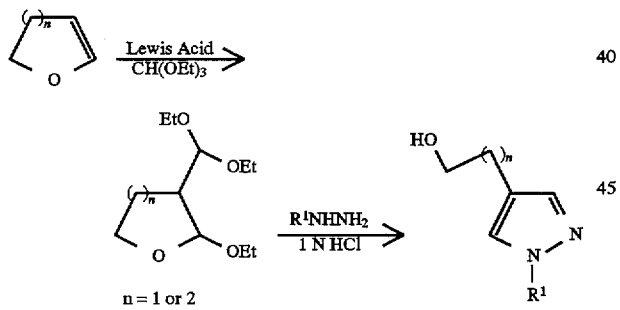

4,5-Dihydrofuran or 3,4-dihydro-2H-pyran is treated with triethylorthoformate in the presence of a Lewis acid, preferably boron trifluoride diethyl etherate, for from 1 to 4 days at ambient temperature. After treating the reaction mixture with an anhydrous base such as potassium carbonate the intermediate diacetal is distilled from the reaction mixture. This diacetal is now treated with an appropriate hydrazine, typically commercially available or synthesized by standard techniques, in aqueous acid at reflux for 4–24 hours. The product is recovered by treatment of the reaction mixture with base and extraction of the base into methylene chloride. The alcohol so recovered is suitable for use without further purification. When $R^1$ is hydrogen, the alcohol can be further modified by direct alkylation of one of the pyrazole nitrogens as described below.

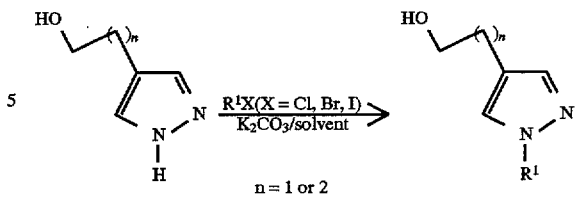

The alkylation is performed in a suitable solvent, typically dimethylformamide, acetonitrile or acetone, with potassium carbonate and the desired alkylating agent. The alkylating agent is a lower alkyl halide, preferably the bromide or iodide. The reaction is performed at ambient to reflux temperature for 1 hour to 3 days.

The 2-(3-pyrrolyl)ethanol was prepared by the method described in *J. Org. Chem.*, 55(26), 6317–28 (1990). Briefly, the anion of pyrrole, generated by treatment with sodium hydride, was silylated with trimethylsilyl chloride in dimethylformamide. The N-silylated pyrrole was then brominated in the 3-position with N-bromosuccinimide in tetrahydrofuran. The 3-bromo intermediate was lithiated with t-butyl lithium and the anion quenched with ethylene oxide. Finally, the N-silyl group was removed with tetrabutylammonium fluoride to give the desired 2-(3-pyrrolyl)ethanol.

Compounds of this invention may alternatively be prepared by N-acylation of the 3-(1,2,3,6-tetrahydro-4-pyridinyl)-1H-indoles or the 3-(piperidin-4-yl)-1H-indoles with an appropriate acylating agent followed by reduction of the resulting amide as described in the following scheme.

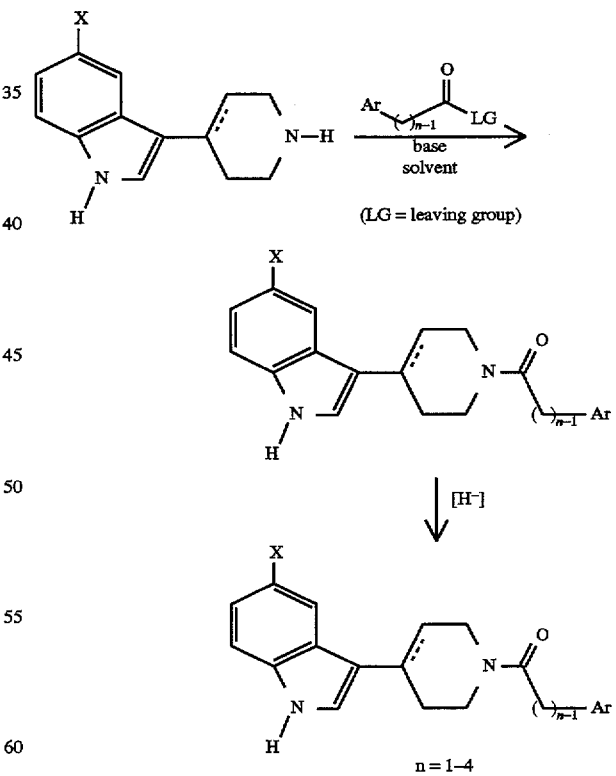

The 3-(1,2,3,6-tetrahydro-4-pyridinyl)-1H-indoles or the 3-(piperidin-4-yl)-1H-indoles are acylated in a suitable solvent such as dimethylformamide or N-methyl-2-pyrrolidinone with an appropriate acyl halide, preferably an acyl chloride, or an activated ester well known in the synthesis of peptides such as the esters of pentafluorophenol or 2,4,5-trichlorophenol. When an acyl halide is used a suitable base, preferably potassium carbonate, is also required in the reaction mixture to neutralize the acid that is formed as the reaction progresses. The reactions are typically performed at ambient to 80° C. for from one hour to three days. The amide prepared in this reaction is then reduced to a compound of this invention with a suitable hydride reducing agent, such as lithium aluminum hydride, aluminum hydride, sodium aluminum hydride, borane tetrahydrofuran complex or borane dimethylsulfide complex, in an anhydrous ethereal solvent such as tetrahydrofuran or diethyl ether. The reaction is typically run at reflux for from 1 to 24 hours. The desired products are recovered by decomposition of the intermediate complexes by the addition of water followed by extraction into a suitable solvent such as ethyl acetate, diethyl ether or dichloromethane.

When a hydroxy substituted compound of this invention is desired, it is easily prepared by catalytic O-debenzylation of the corresponding benzyloxy compound. Furthermore, compounds of this invention which contain a benzyl group on a nitrogen atom of the pyrazolyl or pyrrolyl moiety may be N-debenzylated to give other compounds of this invention. These hydrogenolyses may be performed by dissolution of the substrate in a lower alkanol, such as methanol or ethanol, tetrahydrofuran or a mixed solvent system of tetrahydrofuran and ethyl acetate. The hydrogenation may be performed at an initial hydrogen pressure of 20–80 p.s.i., preferably from 50–60 p.s.i., at 0°–60° C., preferably at ambient temperature to 40° C., for 1 hour to 3 days. Additional charges of hydrogen may be required to drive the reaction to completion depending on the specific substrate. Compounds prepared in this manner are isolated by removal of the catalyst by filtration followed by concentration of the reaction solvent under reduced pressure. The product recovered may be purified by chromatography or recrystallization from a suitable solvent if necessary.

It is evident to the skilled artisan that the conditions for hydrogenolysis of an N- or O-benzyl group are identical to those required for the reduction of the 4,5-double bond of the tetrahydropyridines described supra. The hydrogenolysis and double-bond reduction steps, therefore, may be combined if desired. Additionally, the skilled artisan would understand that, where substituents allow, the order of N-alkylation and double-bond reduction is not important.

The following preparations and examples further illustrate the synthesis of the compounds of this invention and are not intended to limit the scope of the invention in any way. The compounds described below were identified by various standard analytical techniques as stated in the individual preparations and examples.

All of the 3-[1,2,3,6-tetrahydro-4-pyridinyl]-1H-indoles useful as intermediates for compounds of this invention may be prepared as described in the following procedure.

PREPARATION I 5-bromo-3-<1,2,3,6-tetrahydro-4-pyridinyl>-1H-indole

To a solution of 4.29 gm (77 mMol) potassium hydroxide in 50 mL methanol were added 5.0 gm (26 mMol) 5-bromoindole and 7.84 gm (51 mMol) 4-piperidone.HCl.H$_2$O and the reaction mixture was stirred for 18 hours at reflux under a nitrogen atmosphere. The reaction mixture was cooled to ambient temperature, diluted with 500 mL water and the mixture extracted well with dichloromethane. The combined organic extracts were washed with water followed by saturated aqueous sodium chloride and dried over sodium sulfate. The remaining organics were concentrated under reduced pressure to give 6.23 gm (86.5%) of the title compound as a yellow oil.

$^1$H-NMR(DMSO-d$_6$): δ8.00 (s, 1H); 7.40 (s, 1H); 7.30(d, 1H); 7.20 (d, 1H); 6.10 (s, 1H); 3.35 (br s, 2H); 2.85 (m, 2H); 2.35 (br s, 2H).

All of the 3-[piperidin-4-yl]-1H-indoles useful as intermediates for compounds of this invention may be prepared as described in the following procedure.

PREPARATION II 5-bromo-3-[piperidin-4-yl]-1H-indole

To a solution of 13.61 gm (49 mMol) 5-bromo-3-<1,2,3, 6-tetrahydro-4-pyridinyl>-1H-indole in 75 mL 2:1 tetrahydrofuran:ethyl acetate were added 8.0 gm 3% sulfided platinum on carbon and 4.0 gm platinum oxide. The reaction mixture was hydrogenated with an initial hydrogen pressure of 60 p.s.i. at 40° C. for 18 hours and then at ambient temperature for 30 hours. The reaction mixture was filtered and the filtrate concentrated under reduced pressure to give 10.33 gm (75.6%) of the title compound as a light yellow solid.

MS(m/e): 278 (M$^+$).

$^1$H-NMR(DMSO-d$_6$): δ10.6 (s, 1H); 7.2 (d, 1H); 7.05 (s, 2H); 6.7 (d, 1H); 3.15 (s, 1H); 3.05 (s, 1H); 2.8 (m, 3H), 1.95 (s, 1H); 1.85 (s, 1H); 1.6 (m, 2H).

PREPARATION III 5-carboxamidoindole

To a solution of 8.06 gm (50 mMol) indole-5-carboxylic acid in 150 mL dimethylformamide were added 8.11 gm (50 mMol) carbonyldiimidazole and the reaction mixture stirred at ambient temperature for 3 hours. The reaction mixture was then added dropwise to 150 mL concentrated ammonium hydroxide and the reaction mixture was stirred for 18 hours at ambient temperature. The reaction mixture was concentrated under reduced pressure to give a viscous oil which was subjected to silica gel chromatograpy, eluting with a gradient of dichloromethane containing 0–10% methanol. Fractions shown to contain product were combined and concentrated under reduced pressure to give the title compound as an oil which crystallizes upon standing.

$^1$H-NMR(CDCl$_3$): δ8.18 (s, 1H); 7.74 (d, 1H); 7.45 (d, 1H); 7.35 (s, 1H); 6.65 (s, 1H ).

The following preparation is typical of procedures for the synthesis of 2-(3-pyrazolyl)-1-ethanols and 3-(3-pyrazolyl) -1-propanols required for the synthesis of compounds of this invention.

Preparation IV 2-(1-methyl-1H-pyrazol-3-yl)-1-ethanol

To a mixture of 200 gm (2.85 mole) 2,3-dihydrofuran and 800 mL (4.81 mole) triethylorthoformate were added 0.8 mL (6.5 mMol) boron trifluoride diethyl etherate dropwise. After an initial exotherm the reaction mixture was allowed to stir at ambient temperature for four days. To the reaction mixture was then added 4.0 gm potassium carbonate and the reaction mixture was distilled under 6.0 mm Hg. Fractions distilling between 60° C. and 130° C. were collected to give 261.64 gm (42.1%) of a light yellow oil.

MS(m/e): 219(M$^+$)

To a solution of 87.2 gm (0.40 mole) of the previously prepared yellow oil in 787 mL 1N HCl were added 21.3 mL (0.40 mole) methyl hydrazine and the reaction mixture was stirred at reflux for four hours. The reaction mixture was cooled to ambient temperature and the volatiles were removed under reduced pressure. The residual oil was treated with 2N NaOH until basic and the aqueous extracted well with dichloromethane. The combined organic extracts were dried over sodium sulfate and concentrated under reduced pressure to give 32.15 gm (64.5%) of the title compound as a brown oil.

MS(m/e): 126 (M$^+$)

$^1$H-NMR(DMSO-d$_6$): δ7.45 (s, 1H); 7.25 (s, 1H); 4.65 (t, 1H); 3.75 (s, 3H); 3.55 (m, 2H); 2.55 (t, 2H).

Preparation V 2-(1-isopropyl-1H-pyrazol-3-yl)-1-ethanol

To a solution of 1.0 gm (9.0 mMol) 2-(3-pyrazolyl)-1-ethanol in 36 mL dimethylformamide were added 2.38 gm (22.5 mMol) sodium carbonate followed by the dropwise addition of a solution of 0.89 mL (9.0 mMol) 2-iodopropane in 8 mL dimethylformamide. The reaction mixture was heated to 100° C. for 18 hours. The reaction mixture was then cooled to ambient and then concentrated under reduced pressure. The residue was partitioned between water and dichloromethane. The organic phase was then washed with water followed by saturated aqueous sodium chloride and was then dried over sodium sulfate. The remaining organics were concentrated under reduced pressure to give 0.36 gm (26.0%) of the title compound as a brown oil.

$^1$H-NMR(DMSO-d$_6$): δ7.50 (s, 1H); 7.25 (s, 1H); 4.60 (t, 1H); 4.40 (m, 1H); 3.50 (m, 2H); 2.55 (t, 2H); 1.35(d, 6H).

EXAMPLE 1

3-<1-<2-<1-methyl-1H-pyrazol-4-yl>ethyl>-4-piperidinyl>-1H-indole hydrochloride

To a solution of 2.0 gm (0.01 mole) 3-(4-piperidinyl)-1H-indole in 50 mL dimethylformamide were added 2.65 gm (0.025 mole) sodium carbonate followed by 2.04 gm (0.01 mole) 1-methyl-4-(2-methanesulfonyloxyethyl)-1H-pyrazole. The resulting mixture was heated at 100° C. for 18 hours under nitrogen. The dimethylformamide was distilled under reduced pressure and the resulting residue was partitioned between water and dichloromethane. The dichloromethane phase was separated, washed sequentially with water and saturated aqueous sodium chloride solution and then dried over sodium sulfate to give 4.0 gm of a brown oil. The brown oil was chromatographed over silica gel, eluting with 95:5 dichloromethane:methanol. Fractions shown to contain product were combined and concentrated under reduced pressure to give 1.87 gm of 3-<2-<1-methyl-1H-pyrazol-4-yl>ethyl>-4-piperidinyl-1H-indole as a yellow oil. The oil was dissolved in a minimal volume of methanol and to it were added 1.21 mL (0.006 mole) 5N HCl To the resulting solution was added ethyl acetate to the point of incipient precipitation. The solid recovered was recrystallized from methanol/ethyl acetate to give 0.95 gm (27.8%) of the title compound as an off-white solid, m.p.=260° C. (dec.).

MS(m/e): 308(M$^+$)

Calculated for C$_{19}$H$_{24}$N$_4$.HCl: Theory: C, 66.17; H, 7.31; N, 16.25. Found: C, 66.42; H, 7.27; N, 16.02.

The compounds of Examples 2–45 were prepared employing the method described in detail in Example 1.

EXAMPLE 2

5-fluoro-3-<1-<2-<1-methyl-1H-pyrazol-4-yl>ethyl>-4-piperidinyl>-1H-indole hydrochloride Using 2.0 gm (9.2 mMol) 5-fluoro-3-(4-piperidinyl)-1H-indole and 1.87 gm (9.2 mMol) 1-methyl-4-(2-methanesulfonyl-oxyethyl)-1H-pyrazole, 1.61 gm (51.1%) of the title compound were recovered as colorless crystals, m.p.=239° C.

MS(m/e): 326(M$^+$)

Calculated for C$_{19}$H$_{23}$N$_4$F.HCl: Theory: C, 62.89; H, 6.67; N, 15.44. Found: C, 62.80; H, 6.85; N, 15.40.

EXAMPLE 3

5-chloro-3-<1-<2-<1-methyl-1H-pyrazol-4-yl>ethyl>-4-piperidinyl>-1H-indole hydrochloride Using 2.0 gm (8.5 mMol) 5-chloro-3-(4-piperidinyl)-1H-indole and 1.73 gm (8.5 mMol) 1-methyl-4-(2-methanesulfonyloxyethyl)-1H-pyrazole, 0.84 gm (26.1%) of the title compound were recovered as a yellow powder, m.p.=251° C.

MS(m/e): 342 (M$^+$)

Calculated for C$_{19}$H$_{23}$N$_4$Cl.HCl: Theory: C, 60.16; H, 6.38; N, 14.77. Found: C, 59.97; H, 6.39; N, 14.73.

EXAMPLE 4

5-bromo-3-<1-<2-<1-methyl-1H-pyrazol-4-yl>ethyl>-4-piperidinyl>-1H-indole oxalate Using 2.0 gm (7.2 mMol) 5-bromo-3-(4-piperidinyl)-1H-indole and 1.47 gm (7.2 mMol) 1-methyl-4-(2-methanesulfonyloxyethyl)-1H-pyrazole, 1.47 gm (52.7%) of 5-bromo-3-<2-<1-methyl-1H-pyrazol-4-yl>ethyl>-4-piperidinyl-1H-indole were recovered as a yellow oil which was then converted to the oxalate salt, m.p.=104° C.

MS(m/e): 386(M$^+$)

Calculated for C$_{19}$H$_{23}$N$_4$Br.C$_2$H$_2$O$_4$: Theory: C, 52.84; H, 5.28; N, 11.74. Found: C, 52.57; H, 5.21; N, 11.46.

EXAMPLE 5

5-methoxy-3-<1-<2-<1-methyl-1H-pyrazol-4-yl>ethyl>-4-piperidinyl>-1H-indole oxalate Using 2.0 gm (8.7 mMol) 5-methoxy-3-(4-piperidinyl)-1H-indole and 1.77 gm (8.7 mMol) 1-methyl-4-(2-methanesulfonyloxyethyl)-1H-pyrazole, 2.09 gm (71.1%) of 5-methoxy-3-<2-<1-methyl-1H-pyrazol-4-yl>ethyl>-4-piperidinyl-1H-indole were recovered as a yellow oil which was then converted to the oxalate salt, m.p.=80° C.

MS(m/e): 338(M$^+$)

Calculated for C$_{20}$H$_{26}$N$_4$O.C$_2$H$_2$O$_4$: Theory: C, 61.67; H, 6.59; N, 13.08. Found: C, 61.93; H, 6.61; N, 12.97.

EXAMPLE 6

3-<1-<2-<1-(1-methylethyl)-1H-pyrazol-4-yl>ethyl>-4-piperidinyl>-1H-indole hydrochloride Using 0.309 gm (1.5 mMol) 3-(4-piperidinyl)-1H-indole and 0.340 gm (1.5 mMol) 1-(1-methylethyl)-4-(2-methanesulfonyloxyethyl)-1H-pyrazole, 0.12 gm (21.5%) of the title compound were recovered as a brown solid, m.p.=152° C.

MS(m/e): 336(M$^+$)

Calculated for $C_{21}H_{28}N_4 \cdot HCl$: Theory: C, 67.63; H, 7.84; N, 15.02. Found: C, 66.92; H, 7.71; N, 14.87.

EXAMPLE 7

5-fluoro-3-<1-<2-<1-(1-methylethyl)-1H-pyrazol-4-yl>ethyl>-4-piperidinyl>-1H-indole oxalate Using 2.0 gm (9.2 mMol) 5-fluoro-3-(4-piperidinyl)-1H-indole and 2.13 gm (9.2 mMol) 1-(methylethyl)-4-(2-methanesulfonyloxyethyl)-1H-pyrazole, 1.86 gm (57.1%) of 5-fluoro-3-<1-<2-<1-(1-methylethyl)-1H-pyrazol-4-yl>ethyl>-4-piperidinyl>-1H-indole were recovered as a yellow oil which was then converted to the oxalate salt, m.p.=94° C.

MS(m/e): 354(M$^+$)

Calculated for $C_{21}H_{27}N_4F \cdot C_2H_2O_4$: Theory: C, 62.15; H, 6.58; N, 12.60. Found: C, 61.92; H, 6.38; N, 12.59.

EXAMPLE 8

5-chloro-3-<1-<2-<1-(1-methylethyl)-1H-pyrazol-4-yl>ethyl>-4-piperidinyl>-1H-indole Using 4.0 gm (17.0 mMol) 5-chloro-3-(4-piperidinyl)-1H-indole and 3.96 gm (17.0 mMol) 1-(1-methylethyl)-4-(2-methanesulfonyloxyethyl)-1-pyrazole, 1.69 gm (26.8%) of the title compound were recovered as a yellow solid from cyclohexane/ethyl acetate, m.p.=155° C.

MS(m/e): 370 (M$^+$)

Calculated for $C_{21}H_{17}N_4Cl$: Theory: C, 68.00; H, 7.34; N, 15.10. Found: C, 67.83; H, 7.40; N, 14.56.

EXAMPLE 9

5-bromo-3-<1-<2-<1-(1-methylethyl)-1H-pyrazol-4-yl>ethyl>-4-piperidinyl>-1H-indole oxalate Using 2.0 gm (7.2 mMol) 5-bromo-3-(4-piperidinyl)-1H-indole and 1.66 gm (7.2 mMol) 1-(1-methylethyl)-4-(2-methanesulfonyloxyethyl)-1H-pyrazole, 0.96 gm (32.1%) of 5-bromo-3-<2-<1-(1-methylethyl)-1H-pyrazol-4-yl>ethyl>-4-piperidinyl-1H-indole were recovered as a yellow oil which was then converted to the oxalate salt, m.p.=100 C.

MS(m/e): 414(M$^+$)

Calculated for $C_{21}H_{27}N_4Br \cdot C_2H_2O_4$: Theory: C, 54.66; H, 5.78; N, 11.09. Found: C, 54.66; H, 5.87; N, 10.99.

EXAMPLE 10

5-methoxy-3-<1-<2-<1-(1-methylethyl)-1H-pyrazol-4-yl>ethyl>-4-piperidinyl>-1H-indole oxalate Using 1.40 gm (6.1 mMol) 5-methoxy-3-(4-piperidinyl)-1H-indole and 1.66 gm (6.1 mMol) 1-(1-methylethyl)-4-(2-methanesulfonyloxyethyl)-1H-pyrazole, 1.40 gm (62.7%) of 5-methoxy-3-<1-<2-<1-(1-methylethyl)-1H-pyrazol-4-yl>ethyl>-4-piperidinyl>-1H-indole were recovered as a brown oil which was then converted to the oxalate salt, m.p.=84° C.

MS(m/e): 366 (M$^+$)

MS(exact mass): Theory for $C_{22}H_{31}N_4O$: 367.2498. Found: 67.2495.

EXAMPLE 11

5-carboxamido-3-<1-<2-<1-(1-methylethyl)-1H-pyrazol-4-yl>ethyl>-4-piperidinyl>-1H-indole Using 2.0 gm (8.2 mMol) 5-carboxamido-3-(4-piperidinyl)-1H-indole and 1.90 gm (8.2 mMol) 1-(1-methylethyl)-4-(2-methanesulfonyloxyethyl)pyrazole, 1.12 gm (36.0%) of the title compound were recovered as a yellow solid, m.p.=125°–135 C.

MS(m/e): 379(M$^+$)

Calculated for $C_{22}H_{29}N_5O$: Theory: C, 69.63; H, 7.70; N, 18.45. Found: C, 69.13; H, 7.77; N, 18.10.

EXAMPLE 12

3-<1-<2-<1-propyl-1H-pyrazol-4-yl>ethyl>-4-piperidinyl>-1H-indole oxalate

Using 2.0 gm (10.0 mMol) 3-(4-piperidinyl)-1H-indole and 2.32 gm (10.0 mMol) 1-propyl-4-(2-methanesulfonyloxyethyl)-1H-pyrazole, 2.10 gm (49.3%) of the title compound were recovered as a pale yellow solid, m.p.=205° C. (dec).

MS(m/e): 336(M$^+$)

Calculated for $C_{21}H_{28}N_4 \cdot C_2H_2O_4$: Theory: C, 64.77; H, 7.09; N, 13.14. Found: C, 64.84; H, 7.03; N, 13.08.

EXAMPLE 13

5-fluoro-3-<1-<2-<1-propyl-1H-pyrazol-4-yl>ethyl>-4-piperidinyl>-1H-indole oxalate Using 2.0 gm (9.2 mMol) 5-fluoro-3-(4-piperidinyl)-1H-indole and 2.13 gm (9.2 mMol) 1-propyl-4-(2-methanesulfonyloxyethyl)-1H-pyrazole, 1.23 gm (37.8%) of the title compound were recovered as a yellow solid, m.p.=85° C. (dec).

MS(m/e): 354(M$^+$)

Calculated for $C_{21}H_{27}N_4F \cdot C_2H_2O_4$: Theory: C, 62.15; H, 6.58; N, 12.62. Found: C, 62.39; H, 6.64; N, 12.59.

EXAMPLE 14

5-chloro-3-<1-<2-<1-propyl-1H-pyrazol-4-yl>ethyl>-4-piperidinyl>-1H-indole oxalate Using 2.0 gm (8.5 mMol) 5-chloro-3-(4-piperidinyl)-1H-indole and 1.98 gm (8.5 mMol) 1-propyl-4-(2-methanesulfonyloxyethyl)-1H-pyrazole, 0.89 gm (22.7%) of the title compound were recovered as a yellow solid, m.p.=210° C. (dec).

MS(m/e): 370(M$^+$)

Calculated for $C_{21}H_{27}N_4Cl \cdot C_2H_2O_4$: Theory: C, 59.93; H, 6.34; N, 12.15. Found: C, 59.64; H, 6.44; N, 11.97.

EXAMPLE 15

5-bromo-3-<1-<2-<1-propyl-1H-pyrazol-4-yl>ethyl>-4-piperidinyl>-1H-indole oxalate Using 2.0 gm (7.2 mMol) 5-bromo-3-(4-piperidinyl)-1H-indole and 1.66 gm (7.2 mMol) 1-propyl-4-(2-methanesulfonyloxyethyl)-1H-pyrazole, 1.21 gm (33.3%) of the title compound were recovered as a yellow solid, m.p.=101° C.

MS(m/e): 414(M$^+$)

Calculated for $C_{21}H_{27}N_4Cl \cdot C_2H_2O_4$: Theory: C, 54.66; H, 5.78; N, 11.09. Found: C, 54.50; H, 5.66; N, 10.79.

EXAMPLE 16

3-<1-<2-<1-cyclohexyl-1H-pyrazol-4-yl>ethyl>-4-piperidinyl>-1H-indole oxalate

Using 2.54 gm (13.0 mMol) 3-(4-piperidinyl)-1H-indole and 3.45 gm (13.0 mMol) 1-cyclohexyl-4-(2- methanesulfonyloxyethyl)-1H-pyrazole, 1.59 gm (26.2%) of the title compound were recovered as yellow crystals, m.p.=147°–150° C. (methanol).

MS(m/e): 376(M$^+$)

Calculated for $C_{24}H_{32}N_4 \cdot C_2H_2O_4$: Theory: C, 66.93; H, 7.34; N, 12.01. Found: C, 66.95; H, 7.30; N, 12.06.

EXAMPLE 17

5-fluoro-3-<1-<2-<1-cyclohexyl-1H-pyrazol-4-yl>ethyl>-4-piperidinyl>-1H-indole oxalate Using 2.16 gm (9.9 mMol) 5-fluoro-3-(4-piperidinyl)-1H-indole and 2.69 gm (9.9 mMol) 1-cyclohexyl-4-(2-methanesulfonyloxyethyl)-1H-pyrazole, 1.78 gm (37.1%) of the title compound were recovered as yellow crystals, m.p.=197°–199° C. (methanol).

MS(m/e): 394(M$^+$)

Calculated for $C_{24}H_{31}N_4F \cdot C_2H_2O_4$: Theory: C, 64.45; H, 6.86; N, 11.56. Found: C, 64.37; H, 7.01; N, 11.43.

EXAMPLE 18

5-chloro-3-<1-<2-<1-propyl-1H-pyrazol-4-yl>ethyl>-4-piperidinyl>-1H-indole oxalate Using 2.13 gm (9.1 mMol) 5-chloro-3-(4-piperidinyl)-1H-indole and 2.47 gm (9.1 mMol) 1-cyclohexyl-4-(2-methanesulfonyloxyethyl)-1H-pyrazole, 0.96 gm (21.1%) of the title compound were recovered as off-white crystals, m.p.=162°–164° C.

MS(m/e): 410(M$^+$)

Calculated for $C_{24}H_{31}N_4Cl \cdot C_2H_2O_4$: Theory: C, 62.33; H, 6.64; N, 11.18. Found: C, 62.48; H, 6.89; N, 11.04.

EXAMPLE 19

5-bromo-3-<1-<2-<1-propyl-1H-pyrazol-4-yl>ethyl>-4-piperidinyl>-1H-indole oxalate Using 2.0 gm (7.2 mMol) 5-bromo-3-(4-piperidinyl)-1H-indole and 1.95 gm (7.2 mMol) 1-cyclohexyl-4-(2-methanesulfonyloxyethyl)-1H-pyrazole, 0.96 gm (24.5%) of the title compound were recovered as a yellow foam, m.p.=124° C.

MS(m/e): 456(M$^+$)

Calculated for $C_{24}H_{31}N_4Br \cdot C_2H_2O_4$: Theory: C, 57.25; H, 6.10; N, 10.27. Found: C, 57.51; H, 6.13; N, 10.27.

EXAMPLE 20

5-fluoro-3-<1-<2-<1-cyclopropylmethyl-1H-pyrazol-4-yl>ethyl>-4-piperidinyl>-1H-indole hydrochloride Using 1.50 gm (7.0 mMol) 5-fluoro-3-(4-piperidinyl)-1H-indole and 1.70 gm (7.0 mMol) 1-cyclopropylmethyl-4-(2-methanesulfonyloxyethyl)-1H-pyrazole, 1.60 gm (56.7%) of the title compound were recovered from acetonitrile, m.p.=160°–165° C. (dec).

MS(exact mass): Theory for $C_{22}H_{28}N_4F$: 367.2298. Found: 367.2315.

EXAMPLE 21

5-chloro-3-<1-<2-<1-cyclopropylmethyl-1H-pyrazol-4-yl>ethyl>-4-piperidinyl>-1H-indole hydrochloride Using 1.40 gm (6.1 mMol) 5-chloro-3-(4-piperidinyl)-1H-indole and 1.50 gm (6.1 mMol) 1-cyclopropylmethyl-4-(2-methanesulfonyloxyethyl)-1H-pyrazole, 1.10 gm (43.0%) of the title compound were recovered from acetonitrile, m.p.=130°–135° C. (dec).

MS(exact mass): Theory for $C_{22}H_{28}N_4Cl$: 383.002. Found: 383.2019.

EXAMPLE 22

5-fluoro-3-<1-<2-<1-benzyl-1H-pyrazol-4-yl>ethyl>-4-piperidinyl>-1H-indole hydrochloride Using 2.50 gm (9.32 mMol) 5-fluoro-3-(4-piperidinyl)-1H-indole and 1.70 gm (7.0 mMol) 1-benzyl-4-(2-methanesulfonyloxyethyl)1H-pyrazole, 2.5 gm (66.6%) of 5-fluoro-3-<2-<1-benzyl-1H-pyrazol-4-yl>ethyl>-4-piperidinyl-1H-indole were recovered and then converted to the hydrochloride salt. The title compound was recovered from acetonitrile as a foam, m.p.=230°–234° C.

MS(exact mass): Theory for $C_{25}H_{28}N_4F$: 403.2298. Found: 403.2319.

EXAMPLE 23

3-<1-<2-<1-phenyl-1H-pyrazol-4-yl>ethyl>-4-piperidinyl>-1H-indole hydrochloride

Using 2.0 gm (10.0 mMol) 3-(4-piperidinyl)-1H-indole and 2.66 gm (10.0 mMol) 1-phenyl-4-(2-methanesulfonyloxyethyl)-1H-pyrazole, 1.83 gm (46.0%) of the title compound were recovered as light brown crystals, m.p.=247° C.

MS(m/e): 370(M$^+$)

Calculated for $C_{24}H_{26}N_4 \cdot HCl$: Theory: C, 70.83; H, 6.69; N, 13.77. Found: C, 70.77; H, 6.64; N, 13.50.

EXAMPLE 24

5-fluoro-3-<1-<2-<1-phenyl-1H-pyrazol-4-yl>ethyl>-4-piperidinyl>-1H-indole oxalate Using 2.0 gm (9.2 mMol) 5-fluoro-3-(4-piperidinyl)-1H-indole and 2.45 gm (9.2 mMol) 1-phenyl-4-(2-methanesulfonyloxyethyl)-1H-pyrazole, 1.19 gm (27.1%) of the title compound were recovered as brown crystals from methanol, m.p.=217° C. (dec).

MS(m/e): 388(M$^+$)

Calculated for $C_{24}H_{25}N_4F \cdot C_2H_2O_4$: Theory: C, 65.26; H, 5.69; N, 11.71. Found: C, 65.00; H, 5.76; N, 11.71.

EXAMPLE 25

5-chloro-3-<1-<2-<1-phenyl-1H-pyrazol-4-yl>ethyl>-4-piperidinyl>-1H-indole oxalate Using 2.0 gm (8.5 mMol) 5-chloro-3-(4-piperidinyl)-1H-indole and 2.26 gm (8.5 mMol) 1-phenyl-4-(2-methanesulfonyloxyethyl)-1H-pyrazole, 1.02 gm (24.3%) of the title compound were recovered as yellow crystals from methanol, m.p.=227° C. (dec).

MS(m/e): 404(M$^+$)

Calculated for $C_{24}H_{25}N_4Cl \cdot C_2H_2O_4$: Theory: C, 63.09; H, 5.50; N, 11.32. Found: C, 63.06; H, 5.65; N, 11.38.

EXAMPLE 26

5-bromo-3-<1-<2-<1-phenyl-1H-pyrazol-4-yl>ethyl>-4-piperidinyl>-1H-indole oxalate Using 2.0 gm (7.2 mMol) 5-bromo-3-(4-piperidinyl)-1H-indole and 1.92 gm (7.2 mMol) 1-phenyl-4-(2- methanesulfonyloxyethyl)-1H-pyrazole, 1.65 gm (42.5%) of the title compound were recovered as off-white crystals from methanol, m.p.=217° C. (dec).

MS(m/e): 450 (M$^+$)

Calculated for $C_{24}H_{25}N_4Br.C_2H_2O_4$: Theory: C, 57.89; H, 5.04; N, 10.39. Found: C, 58.09; H, 5.19; N, 10.53.

EXAMPLE 27

5-methoxy-3-<1-<2-<1-phenyl-1H-pyrazol-4-yl>ethyl>-4-piperidinyl>-1H-indole oxalate Using 2.0 gm (8.7 mMol) 5-methoxy-3-(4-piperidinyl)-1H-indole and 2.31 gm (8.7 mMol) 1-phenyl-4-(2-methanesulfonyloxyethyl)-1H-pyrazole, 2.24 gm (64.4%) of 5-methoxy-3-<1-<2-<1-phenyl-1H-pyrazol-4-yl>ethyl>-4-piperidinyl>-1H-indole were recovered as a yellow oil which was converted to the title compound, m.p.=98° C.

MS(m/e): 400(M$^+$)

Calculated for $C_{25}H_{28}N_4O.C_2H_2O_4$: Theory: C, 66.11; H, 6.16; N, 11.42. Found: C, 65.90; H, 6.05; N, 11.20.

EXAMPLE 28

5-carboxamido-3-<1-<2-<1-phenyl-1H-pyrazol-4-yl>ethyl>-4-piperidinyl>-1H-indole

Using 2.0 gm (8.2 mMol) 5-carboxamido-3-(4-piperidinyl)-1H-indole and 2.19 gm (8.2 mMol) 1-phenyl-4-(2-methanesulfonyloxyethyl)-1H-pyrazole, 0.91 gm (26.8%) of the title compound were recovered as tan crystals from methanol, m.p.=207° C.

MS(m/e): 413 (M$^+$)

Calculated for $C_{25}H_{27}N_5O$: Theory: C, 72.61; H, 6.58; N, 16.94. Found: C, 72.36; H, 6.66; N, 16.64.

EXAMPLE 29

5-chloro-3-<1-<2-<1-(2-fluorophenyl)-1H-pyrazol-4-yl>ethyl>-4-piperidinyl>-1H-indole Using 2.0 gm (8.5 mMol) 5-chloro-3-(4-piperidinyl)-1H-indole and 2.43 gm (8.5 mMol) 1-(2-fluorophenyl)-4-(2-methanesulfonyloxyethyl)-1H-pyrazole, 1.50 gm (41.8%) of the title compound were recovered as yellow crystals from methanol, m.p.=207° C.

MS(m/e): 422 (M$^+$)

Calculated for $C_{24}H_{24}N_4ClF$: Theory: C, 68.16; H, 5.72; N, 13.25. Found: C, 68.37; H, 5.80; N, 13.34.

EXAMPLE 30

5-chloro-3-<1-<2-<1-(3-fluorophenyl)-1H-pyrazol-4-yl>ethyl>-4-piperidinyl>-1H-indole oxalate Using 2.0 gm (8.5 mMol) 5-chloro-3-(4-piperidinyl)-1H-indole and 2.43 gm (8.5 mMol) 1-(3-fluorophenyl)-4-(2-methanesulfonyloxyethyl)-1H-pyrazole, 1.32 gm (30.3%) of the title compound were recovered as a brown solid from methanol, m.p.=211° C. (dec).

MS(m/e): 422(M$^+$)

Calculated for $C_{24}H_{24}N_4ClF.C_2H_2O_4$: Theory: C, 60.88; H, 5.11; N, 10.92. Found: C, 61.16; H, 5.21; N, 10.94.

EXAMPLE 31

5-chloro-3-<1-<2-<1-(4-fluorophenyl)-1H-pyrazol-4-yl>ethyl>-4-piperidinyl>-1H-indole oxalate Using 2.0 gm (8.5 mMol) 5-chloro-3-(4-piperidinyl)-1H-indole and 2.43 gm (8.5 mMol) 1-(4-fluorophenyl)-4-(2-methanesulfonyloxyethyl)-1H-pyrazole, 0.98 gm (22.5%) of the title compound were recovered, m.p.=112° C.

MS(m/e): 422(M$^+$)

Calculated for $C_{24}H_{24}N_4ClF.C_2H_2O_4$: Theory: C, 60.88; H, 5.11; N, 10.92. Found: C, 60.66; H, 4.98; N, 10.95.

EXAMPLE 32

5-chloro-3-<1-<2-<1-(2-chlorophenyl)-1H-pyrazol-4-yl>ethyl>-4-piperidinyl>-1H-indole oxalate Using 2.0 gm (8.5 mMol) 5-chloro-3-(4-piperidinyl)-1H-indole and 2.56 gm (8.5 mMol) 1-(2-chlorophenyl)-4-(2-methanesulfonyloxyethyl)-1H-pyrazole, 1.10 gm (24.5%) of the title compound were recovered as yellow crystals from methanol, m.p.=177°–178° C.

MS(m/e): 438(M$^+$)

Calculated for $C_{24}H_{24}N_4Cl_2.C_2H_2O_4$: Theory: C, 58.99; H, 4.95; N, 10.58. Found: C, 59.11; H, 4.95; N, 10.53.

EXAMPLE 33

5-chloro-3-<1-<2-<1-(3-chlorophenyl)-1H-pyrazol-4-yl>ethyl>-4-piperidinyl>-1H-indole oxalate Using 2.0 gm (8.5 mMol) 5-chloro-3-(4-piperidinyl)-1H-indole and 2.56 gm (8.5 mMol) 1-(3-chlorophenyl)-4-(2-methanesulfonyloxyethyl)-1H-pyrazole, 1.11 gm (24.5%) of the title compound were recovered as a yellow solid from methanol, m.p.=235° C. (dec).

MS(m/e): 438(M$^+$)

Calculated for $C_{24}H_{24}N_4Cl_2.C_2H_2O_4$: Theory: C, 58.99; H, 4.95; N, 10.58. Found: C, 58.77; H, 4.88; N, 10.54.

EXAMPLE 34

5-chloro-3-<1-<2-<1-(4-chlorophenyl)-1H-pyrazol-4-yl>ethyl>-4-piperidinyl>-1H-indole Using 2.0 gm (8.5 mMol) 5-chloro-3-(4-piperidinyl)-1H-indole and 2.56 gm (8.5 mMol) 1-(4-chlorophenyl)-4-(2-methanesulfonyloxyethyl)-1H-pyrazole, 0.72 gm (19.3%) of the title compound were recovered as a yellow solid from methanol, m.p.=105° C.

MS(m/e): 438(M$^+$)

Calculated for $C_{24}H_{24}N_4Cl_2$: Theory: C, 65.61; H, 5.51; N, 12.75. Found: C, 65.36; H, 5.71; N, 12.58.

EXAMPLE 35

5-chloro-3-<1-<2-<1-(2-bromophenyl)-1H-pyrazol-4-yl>ethyl>-4-piperidinyl>-1H-indole oxalate Using 2.89 gm (12.0 mMol) 5-chloro-3-(4-piperidinyl)-1H-indole and 4.25 gm (12.0 mMol) 1-(2-bromophenyl)-4-(2-methanesulfonyloxyethyl)-1H-pyrazole, 2.13 gm (31.0%) of the title compound were recovered as a light brown solid from methanol, m.p.=108° C.

MS(m/e): 484(M$^+$)

Calculated for $C_{24}H_{24}N_4ClBr.C_2H_2O_4$: Theory: C, 54.42; H, 4.57; N, 9.76. Found: C, 54.71; H, 4.53; N, 9.61.

EXAMPLE 36

5-chloro-3-<1-<2-<1-(3-bromophenyl)-1H-pyrazol-4-yl>ethyl>-4-piperidinyl>-1H-indole oxalate Using 2.0 gm (8.5 mMol) 5-chloro-3-(4-piperidinyl)-1H-indole and 2.94 gm (8.5 mMol) 1-(3-bromophenyl)-4-(2- methanesulfonyloxyethyl)-1H-pyrazole, 2.19 gm (44.9%) of the title compound were recovered as off-white crystals from methanol, m.p.=232° C.

MS(m/e): 484(M+)

Calculated for $C_{24}H_{24}N_4ClBr.C_2H_2O_4$: Theory: C, 54.42; H, 4.57; N, 9.76. Found: C, 54.19; H, 4.70; N, 9.58.

EXAMPLE 37

5-chloro-3-<1-<2-<1-(4-bromophenyl)-1H-pyrazol-4-yl>ethyl>-4-piperidinyl>-1H-indole Using 2.0 gm (8.5 mMol) 5-chloro-3-(4-piperidinyl)-1H-indole and 2.94 gm (8.5 mMol) 1-(4-bromophenyl)-4-(2-methanesulfonyloxyethyl)-1H-pyrazole, 0.76 gm (18.4%) of the title compound were recovered as a yellow solid from methanol, m.p.=100° C.

MS(m/e): 485(M+)

Calculated for $C_{24}H_{24}N_4ClBr$: Theory: C, 59.58; H, 5.00; N, 11.58. Found: C, 59.41; H, 5.06; N, 11.73.

EXAMPLE 38

5-chloro-3-<1-<2-<1-(4-iodophenyl)-1H-pyrazol-4-yl>ethyl>-4-piperidinyl>-1H-indole oxalate Using 2.0 gm (8.5 mMol) 5-chloro-3-(4-piperidinyl)-1H-indole and 3.34 gm (8.5 mMol) 1-(4-iodophenyl)-4-(2-methanesulfonyloxyethyl)-1H-pyrazole, 0.55 gm (10.4%) of the title compound were recovered as a tan solid from methanol, m.p.=150° C.

MS(m/e): 531(M+)

Calculated for $C_{24}H_{24}N_4ClI.C_2H_2O_4$: Theory: C, 50.30; H, 4.22; N, 9.02. Found: C, 50.56; H, 4.12; N, 9.19.

EXAMPLE 39

5-chloro-3-<1-<2-<1-(2-methoxyphenyl)-1H-pyrazol-4-yl>ethyl>-4-piperidinyl>-1H-indole oxalate Using 1.29 gm (5.5 mMol) 5-chloro-3-(4-piperidinyl)-1H-indole and 1.63 gm (5.5 mMol) 1-(2-methoxyphenyl)-4-(2-methanesulfonyloxyethyl)-1H-pyrazole, 0.36 gm (12.4%) of the title compound were recovered as yellow crystals from methanol, m.p.=150°–153° C. (dec).

MS(m/e): 434(M+)

Calculated for $C_{25}H_{27}N_4O.C_2H_2O_4$: Theory: C, 61.77; H, 5.57; N, 10.67. Found: C, 62.01; H, 5.71; N, 10.96.

EXAMPLE 40

5-chloro-3-<1-<2-<1-(4-methoxyphenyl)-1H-pyrazol-4-yl>ethyl>-4-piperidinyl>-1H-indole Using 2.0 gm (8.5 mMol) 5-chloro-3-(4-piperidinyl)-1H-indole and 2.53 gm (8.5 mMol) 1-(4-methoxyphenyl)-4-(2-methanesulfonyloxyethyl)-1H-pyrazole, 0.76 gm (20.6%) of the title compound were recovered as brown crystals, m.p.=100° C.

MS(m/e): 485(M+)

Calculated for $C_{25}H_{27}N_4OCl$: Theory: C, 69.03; H, 6.26; N, 12.88. Found: C, 69.30; H, 6.18; N, 12.98.

EXAMPLE 41

5-chloro-3-<1-<2-<1-(2-methylphenyl)-1H-pyrazol-4-yl>ethyl>-4-piperidinyl>-1H-indole oxalate Using 2.0 gm (8.5 mMol) 5-chloro-3-(4-piperidinyl)-1H-indole and 2.4 gm (8.5 mMol) 1-(2-methylphenyl)-4-(2-methanesulfonyloxyethyl)-1H-pyrazole, 0.96 gm (21.9%) of the title compound were recovered, m.p.=105° C.

MS(m/e): 418(M+)

Calculated for $C_{25}H_{27}N_4Cl.C_2H_2O_4$: Theory: C, 63.71; H, 5.74; N, 11.01. Found: C, 63.99; H, 5.76; N, 11.04.

EXAMPLE 42

5-chloro-3-<1-<2-<1-(3-methylphenyl)-1H-pyrazol-4-yl>ethyl>-4-piperidinyl>-1H-indole oxalate Using 2.0 gm (8.5 mMol) 5-chloro-3-(4-piperidinyl)-1H-indole and 2.39 gm (8.5 mMol) 1-(3-methylphenyl)-4-(2-methanesulfonyloxyethyl)-1H-pyrazole, 0.98 gm (22.6%) of the title compound were recovered as brown crystals from methanol, m.p.=231° C. (dec).

MS(m/e): 418(M+)

Calculated for $C_{25}H_{27}N_4Cl.C_2H_2O_4$: Theory: C, 63.71; H, 5.74; N, 11.01. Found: C, 63.48; H, 5.80; N, 11.22.

EXAMPLE 43

5-chloro-3-<1-<2-<1-(4-methylphenyl)-1H-pyrazol-4-yl>ethyl>-4-piperidinyl>-1H-indole Using 2.0 gm (8.5 mMol) 5-chloro-3-(4-piperidinyl)-1H-indole and 2.39 gm (8.5 mMol) 1-(4-methylphenyl)-4-(2-methanesulfonyloxyethyl)-1H-pyrazole, 0.82 gm (23.0%) of the title compound were recovered as a yellow solid from methanol, m.p.=99° C.

MS(m/e): 418(M+)

Calculated for $C_{25}H_{27}N_4Cl$: Theory: C, 71.67; H, 6.50; N, 13.37. Found: C, 71.78; H, 6.58; N, 13.16.

EXAMPLE 44

5-fluoro-3-<1-<2-<1H-pyrrol-3-yl>ethyl>-4-piperidinyl>-1H-indole oxalate

Using 1.19 gm (5.4 mMol) 5-fluoro-3-(4-piperidinyl)-1H-indole and 1.03 gm (5.4 mMol) 3-(2-methanesulfonyloxyethyl)-1H-pyrrole, 0.24 gm (11.1%) of the title compound were recovered, m.p.=84° C.

MS(m/e): 311(M+)

Calculated for $C_{19}H_{22}N_3F.C_2H_2O_4$: Theory: C, 62.83; H, 6.03; N, 10.47. Found: C, 62.80; H, 5.95; N, 10.31.

EXAMPLE 45

5-fluoro-3-<1-<2-<pyridin-2-yl>ethyl>-4-piperidinyl>-1H-indole dihydrochloride

Using 1.0 gm (3.73 mMol) 5-fluoro-3-(4-piperidinyl)-1H-indole and 0.90 gm (4.5 mMol) 2-(2-methanesulfonyloxyethyl)-pyridine, 0.90 gm (60.9%) of the title compound were recovered as a crystalline solid from isopropanol, m.p.=214°–220° C.

MS(m/e): 324(M+)

Calculated for $C_{20}H_{22}N_3F.2HCl$: Theory: C, 60.61; H, 6.10; N, 10.60. Found: C, 60.82; H, 6.31; N, 10.76.

EXAMPLE 46

5-fluoro-3-<1-<2-<pyridin-4-yl>ethyl>-4-piperidinyl>-1H-indole dihydrochloride

A solution of 1.0 gm (3.73 mMol) 5-fluoro-3-(4-piperidinyl)-1H-indole and 2.4 gm (7.5 mMol) 3,4,6- trichlorophenoxy 2-(4-pyridinyl)acetate in 40 mL dimethylformamide were stirred at ambient temperature for 18 hours under a nitrogen atmosphere. The reaction mixture was concentrated under reduced pressure and the residue partitioned between ethyl acetate and aqueous sodium bicarbonate solution. The phases were separated and the organic extract dried over sodium sulfate then concentrated under reduced pressure. The resultant oil was subjected to silica gel chromatography, eluting with a gradient of ethyl acetate containing 0–5% methanol. Fractions shown to contain the desired amide were combined and concentrated under reduced pressure to give 5-fluoro-3-[1-(2-(4-pyridinyl)acetyl)-4-piperidinyl]-1H-indole as a colorless solid.

A solution of 1.33 gm (3.94 mMol) 5-fluoro-3-[1-(2-(4-pyridinyl)acetyl)-4-piperidinyl]-1H-indole in 20 mL tetrahydrofuran was heated to reflux under a nitrogen atmosphere while 3.3 mL (6.57 mMol) borane.methylsulfide complex (2.0M in tetrahydrofuran) were added dropwise. After one hour the colorless suspension was cautiously quenched by the addition of 15 mL water and the tetrahydrofuran was then removed by distillation. The aqueous pot residue was allowed to cool to ambient and was then made basic with ammonium hydroxide and extracted well with ethyl acetate. The organic phases were combined, dried over sodium sulfate and concentrated under reduced pressure. The residue was subjected to silica gel chromatography, eluting with ethyl acetate. Fractions shown to contain the desired product were combined and concentrated under reduced pressure to give a colorless solid. The solid was dissolved in methanol and one equivalent of 1N HCl were added. The volatiles were removed under reduced pressure and the residue crystallized from methanol to give 0.31 gm (19.8%) of the title compound as a colorless solid, m.p.=196°–200° C.

MS(exact mass): Theory for $C_{20}H_{22}N_3F$: 324.1876. Found: 324.1892.

EXAMPLE 47

5-fluoro-3-<1-<2-<pyridin-3-yl>ethyl>-4-piperidinyl>-1H-indole hydrochloride monohydrate Using the procedure described in detail in Example 46, 0.17 gm (7.6%) of the title compound were recovered as a colorless solid, m.p.=240°–245° C.

MS(m/e): 323(M$^+$)

Calculated for $C_{20}H_{23}N_3F.HCl\ H_2O$: Theory: C, 63.57; H, 6.67; N, 11.12. Found: C, 63.46; H, 6.42; N, 11.38.

EXAMPLE 48

5-fluoro-3-<1-<2-<1H-pyrazol-4-yl>ethyl>-4-piperidinyl>-1H-indole dihydrochloride To a solution of 1.5 gm (3.42 mMol) 5-fluoro-3-<1-<2-<1-benzyl-1H-pyrazol-4-yl>ethyl>-4-piperidinyl>-1H-indole in 50 mL ethanol were added 1.5 gm 5% palladium on carbon. The reaction was stirred at 40° C. for 18 hours at an initial hydrogen pressure of 60 p.s.i. The reaction mixture was filtered and the filtrate concentrated under reduced pressure to give a pale purple oil which crystallized on standing. The residue was treated with excess ethereal hydrogen chloride and the solid crystallized from isopropanol to give 0.65 gm (49.4%) of the title compound as a colorless solid, m.p.=260°–265° C. (dec).

MS(m/e): 313(M$^+$)

Calculated for $C_{18}H_{21}N_4F$. 2HCl: Theory: C, 56.11; H, 6.02; N, 14.54. Found: C, 56.41; H, 6.09; N, 14.61.

EXAMPLE 49

5-hydroxy-3-<1-<2-<1-methyl-1H-pyrazol-4-yl>ethyl>-4-piperidinyl>-1H-indole oxalate To a solution of 2.43 gm (5.9 mMol) 5-benzyloxy-3-<1-<2-<1-methyl-1H-pyrazol-4-yl>ethyl>-4-piperidinyl>-1H-indole in 75 mL ethanol were added 1.0 gm 5% palladium on carbon and the reaction mixture was hydrogenated with an initial hydrogen pressure of 60 p.s.i. at ambient temperature for 18 hours. The reaction mixture was then filtered and the filtrate concentrated under reduced pressure to a tan foam. The residue is dissolved in a minimal volume of methanol and to it are added one equivalent of oxalic acid and the volatiles removed under reduced pressure to give 1.49 gm (60.9%) of the title compound as a gold foam, m.p.=80° C.

MS(m/e): 324(M$^+$)

Calculated for $C_{19}H_{24}N_4O.C_2H_2O_4$: Theory: C, 60.86; H, 6.32; N, 13.52. Found: C, 61.11; H, 6.35; N, 13.31.

The compounds of Examples 50–53 were prepared employing the method described in detail in Example 49.

EXAMPLE 50

5-hydroxy-3-<1-<2-<1-(1-methylethyl)-1H-pyrazol-4-yl>ethyl>-4-piperidinyl>-1H-indole Using 1.95 gm (4.4 mMol) 5-benzyloxy-3-<1,2,3,6-tetrahydro-1-<2-<1-(1-methylethyl)-1H-pyrazol-4-yl>ethyl>-4-pyridinyl>-1H-indole, 0.79 gm (50.9%) of the title compound were recovered as grey crystals from methanol, m.p.=264° C.

MS(m/e): 352(M$^+$)

Calculated for $C_{21}H_{28}N_4O$: Theory: C, 71.56; H, 8.01; N, 15.89. Found: C, 71.55; H, 8.21; N, 15.71.

EXAMPLE 51

5-hydroxy-3-<1-<2-<1-cyclohexyl-1H-pyrazol-4-yl>ethyl>-4-piperidinyl>-1H-indole oxalate Using 1.24 gm (2.6 mMol) 5-benzyloxy-3-<1,2,3,6-tetrahydro-1-<2-<1-cyclohexyl-1H-pyrazol-4-yl>ethyl>-4-pyridinyl>-1H-indole, 0.52 gm (41.1%) of the title compound were recovered as a brown foam, m.p.=91° C.

MS(m/e): 392(M$^+$)

Calculated for $C_{24}H_{32}N_4O.C_2H_2O_4$: Theory: C, 64.72; H, 7.10; N, 11.61. Found: C, 64.93; H, 7.36; N, 11.39.

EXAMPLE 52

5-hydroxy-3-<1-<2-<1-phenyl-1H-pyrazol-4-yl>ethyl>-4-piperidinyl>-1H-indole

Using 2.53 gm (5.3 mMol) 5-benzyloxy-3-<1,2,3,6-tetrahydro-1-<2-<1-phenyl-1H-pyrazol-4-yl>ethyl>-4-pyridinyl>-1H-indole, 1.26 gm (61.6%) of the title compound were recovered as off-white crystals from methanol, m.p.=225°–228° C.

MS(m/e): 386(M$^+$)

Calculated for $C_{24}H_{26}N_4O$: Theory: C, 74.58; H, 6.78; N, 14.50. Found: C, 74.64; H, 7.00; N, 14.19.

EXAMPLE 53

5-hydroxy-3-<1-<2-<1-propyl-1H-pyrazol-4-yl>ethyl>-4-piperidinyl>-1H-indole

Using 1.78 gm (4.0 mMol) 5-benzyloxy-3-<1,2,3,6-tetrahydro-1-<2-<1-propyl-1H-pyrazol-4-yl>ethyl>-4- pyridinyl>-1H-indole, 0.22 gm (15.6%) of the title compound were recovered as light brown crystals from methanol, m.p.=227° C.

MS(m/e): 352(M⁺)

Calculated for $C_{21}H_{28}N_4O$: Theory: C, 71.56; H, 8.01; N, 15.89. Found: C, 71.68; H, 8.05; N, 15.97.

EXAMPLE 54

5-chloro-3-<1-<3-<1H-pyrazol-4-yl>propyl>-4-piperidinyl>-1H-indole oxalate

A mixture of 3.26 gm (14 mMol) 5-chloro-3-(4-piperidinyl)-1H-indole, 2.03 gm (14 mMol) 3-(1H-pyrazol-3-yl)-1-chloropropane and 3.71 gm (35 mMol) sodium carbonate in 76 mL dimethylformamide was heated at 100° C. for 18 hours. The reaction mixture was cooled to ambient and the solvent removed under reduced pressure. The residue was partitioned between water and dichloromethane, then the phases were separated. The organic phase was washed with water followed by saturated aqueous sodium chloride and the remaining organics were dried over sodium sulfate. The dichloromethane was removed under reduced pressure and the residual yellow oil subjected to flash silica gel chromatography, eluting with a gradient system of dichloromethane containing 0–10% methanol. Fractions shown to contain product were concentrated under reduced pressure to give 1.72 gm (35.9%) 5-chloro-3-<1-<3-<1H-pyrazol-4-yl>propyl>-4-piperidinyl>-1H-indole as a colorless foam. The oxalate salt was formed to give the title compound as a light yellow foam. m.p.=110° C.

MS(m/e): 343(M⁺)

Calculated for $C_{19}H_{32}N_4Cl \cdot C_2H_2O_4$: Theory: C, 58.27; H, 5.82; N, 12.94. Found: C, 58.07; H, 5.97; N, 12.88.

EXAMPLE 55

5-chloro-3-<1,2,3,6-tetrahydro-1-<2-<1-(1-ethylmethyl)-1H-pyrazol-4-yl>ethyl>-4-pyridinyl>-1H-indole To a suspension of 13.2 gm (56 mMol) 5-chloro-3-(4-(1,2,3,6-tetrahydropyridinyl)-1H-indole and 16.0 gm (151 mMol) potassium carbonate in 1.5 L acetone were added 9.7 gm (56.2 mMol) 2-(1-(1-methylethyl)-1H-pyrazol-4-yl)-1-chloroethane and the reaction mixture heated at reflux for 48 hours. The reaction mixture was cooled to ambient temperature and the solvent removed under reduced pressure. The residue was treated with dilute aqueous sodium hydroxide and this aqueous mixture extracted well with chloroform. Combined organic phases were washed with water, dried over sodium sulfate and then concentrated under reduced pressure. The residual oil was subjected to silica gel chromatography and fractions shown to contain the desired product concentrated under reduced pressure. The residue was crystallized from chloroform/hexane to give 2.8 gm (13.5%) of the title compound as colorless crystals.

MS(m/e): 368(M⁺)

Calculated for $C_{21}H_{25}N_4Cl$: Theory: C, 68.37; H, 6.83; N, 15.19. Found: C, 68.28; H, 6.82; N, 14.96.

To determine the use of the compounds of this invention in the treatment of migraine, their ability to bind to the 5-$HT_{1F}$ receptor subtype was determined. The ability of the compounds of this invention to bind to the 5-$HT_{1F}$ receptor subtype was measured essentially as described in N. Adham, et al., *Proceedings of the National Academy of Sciences (USA)*, 90, 408–412 (1993).

Membrane Preparation:

Membranes were prepared from transfected Ltk-cells which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford (*Anal. Biochem.*, 72, 248–254 (1976)).

Radioligand Binding:

[³H-5-HT] binding was performed using slight modifications of the 5-$HT_{1D}$ assay conditions reported by Herrick-Davis and Titeler (*J. Neurochem.*, 50, 1624–1631 (1988)) with the omission of masking ligands. Radioligand binding studies were achieved at 37° C. in a total volume of 250 μL of buffer (50 mM Tris, 10 mM $MgCl_2$, 0.2 mM EDTA, 10 μM pargyline, 0.1% ascorbate, pH=7.4 at 37° C.) in 96 well microtiter plates. Saturation studies were conducted using [³H]5-HT at 12 different concentrations ranging from 0.5 nM to 100 nM. Displacement studies were performed using 4.5–5.5 nM [³H]5-HT. The binding profile of drugs in competition experiments was accomplished using 10–12 concentrations of compound. Incubation times were 30 minutes for both saturation and displacement studies based upon initial investigations which determined equilibrium binding conditions. Nonspecific binding was defined in the presence of 10 μM 5-HT. Binding was initiated by the addition of 50 μL membrane homogenates (10–20 μg). The reaction was terminated by rapid filtration through presoaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [³H]5-HT averaged between 45–50%. Binding data was analyzed by computer-assisted nonlinear regression analysis (Accufit and Accucomp, Lunden Software, Chagrin Falls, Ohio). $IC_{50}$ values were converted to $K_i$ values using the Cheng-Prusoff equation (*Biochem. Pharmacol.*, 22, 3099–3108 (1973). All experiments were performed in triplicate. The results of these binding experiments are summarized in Table I.

TABLE I

| COMPOUND OF EXAMPLE NUMBER | 5-$HT_{1F}$ BINDING $K_i$ (nM) | COMPOUND OF EXAMPLE NUMBER | 5-$HT_{1F}$ BINDING $K_i$ (nM) |
|---|---|---|---|
| 1 | 5.7 | 29 | 10.4 |
| 2 | 2.5 | 30 | 51.0 |
| 3 | 1.7 | 31 | 11.5 |
| 4 | 3.0 | 32 | 44.1 |
| 5 | 9.9 | 33 | 85.5 |

TABLE I-continued

| COMPOUND OF EXAMPLE NUMBER | 5-HT$_{1F}$ BINDING K$_i$ (nM) | COMPOUND OF EXAMPLE NUMBER | 5-HT$_{1F}$ BINDING K$_i$ (nM) |
|---|---|---|---|
| 6 | 4.5 | 34 | 160.8 |
| 7 | 4.9 | 35 | 48.4 |
| 8 | 4.1 | 36 | 142.5 |
| 9 | 5.0 | 37 | 65.6 |
| 10 | 6.2 | 38 | 77.4 |
| 11 | 10.3 | 39 | 63.5 |
| 12 | 3.3 | 40 | 12.7 |
| 13 | 6.0 | 41 | 153.0 |
| 14 | 5.7 | 42 | 43.2 |
| 15 | 6.6 | 43 | 37.7 |
| 16 | 43.8 | 44 | 53.9 |
| 17 | 33.2 | 45 | 27.0 |
| 18 | 34.0 | 46 | 5.3 |
| 19 | 49.4 | 47 | 115.0 |
| 20 | 8.9 | 48 | 8.1 |
| 21 | 14.5 | 49 | 1.4 |
| 22 | 52.5 | 50 | 2.3 |
| 23 | 4.3 | 51 | 4.4 |
| 24 | 5.5 | 52 | 2.4 |
| 25 | 6.9 | 53 | 1.1 |
| 26 | 13.8 | 54 | 42.0 |
| 27 | 9.5 | 55 | 7.4 |
| 28 | 24.0 | | |

As was reported by R. L. Weinshank, et al., WO93/14201, the 5-HT$_{1F}$ receptor is functionally coupled to a G-protein as measured by the ability of serotonin and serotonergic drugs to inhibit forskolin stimulated cAMP production in NIH3T3 cells transfected with the 5-HT$_{1F}$ receptor. Adenylate cyclase activity was determined using standard techniques. A maximal effect is achieved by serotonin. An E$_{max}$ is determined by dividing the inhibition of a test compound by the maximal effect and determining a percent inhibition. (N. Adham, et al., supra.; R. L. Weinshank, et al., *Proceedings of the National Academy of Sciences(USA)*, 89,3630–3634 (1992)), and the references cited therein.

Measurement of cAMP formation

Transfected NIH3T3 cells (estimated Bmax from one point competition studies=488 fmol/mg of protein) were incubated in DMEM, 5 mM theophylline, 10 mM HEPES (4-[2-hydroxyethyl]-1-piperazineethanesulfonic acid) and 10 μM pargyline for 20 minutes at 37° C., 5% CO$_2$. Drug dose-effect curves were then conducted by adding 6 different final concentrations of drug, followed immediately by the addition of forskolin (10 μM). Subsequently, the cells were incubated for an additional 10 minutes at 37° C. in 5% CO$_2$. The medium was aspirated and the reaction was stopped by the addition of 100 mM HCl. To demonstrate competitive antagonism, a dose-response curve for 5-HT was measured in parallel, using a fixed dose of methiothepin (0.32 μM). The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software. All of the compounds exemplified were tested and found to be agonists at the 5-HT$_{1F}$ receptor in the cAMP assay.

The discovery that the pain associated with migraine and associated disorders is inhibited by agonists of the 5-HT$_{1F}$ receptor required the analysis of data from diverse assays of pharmacological activity. To establish that the 5-HT$_{1F}$ receptor subtype is responsible for mediating neurogenic meningeal extravasation which leads to the pain of migraine, the binding affinity of a panel of compounds to serotonin receptors was measured first, using standard procedures. For example, the ability of a compound to bind to the 5-HT$_{1F}$ receptor subtype was performed as described supra. For comparison purposes, the binding affinities of compounds to the 5-HT$_{1D\alpha}$, 5-HT$_{1D\beta}$, 5-HT$_{1E}$ and 5-HT$_{1F}$ receptors were also determined as described supra, except that different cloned receptors were employed in place of the 5-HT$_{1F}$ receptor clone employed therein. The same panel was then tested in the cAMP assay to determine their agonist or antagonist character. Finally, the ability of these compounds to inhibit neuronal protein extravasation, a functional assay for migraine pain, was measured.

The panel of compounds used in this study represents distinct structural classes of compounds which were shown to exhibit a wide range of affinities for the serotonin receptors assayed. Additionally, the panel compounds were shown to have a wide efficacy range in the neuronal protein extravasation assay as well. The panel of compounds selected for this study are described below.

Compound I
3-[2-(dimethyamino)ethyl]-N-methyl-1H-indole-5-methanesulfonamide butane-1,4-dioate (1:1)
(Sumatriptan succinate)

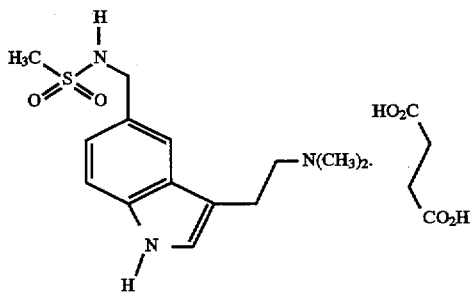

Sumatriptan succinate is commercially available as Imitrex™ or may be prepared as described in U.S. Pat. No. 5,037,845, issued Aug. 6, 1991, which is herein incorporated by reference.

Compound II
5-fluoro-3-<1-<2-<1-methyl-1H-pyrazol-4-yl>ethyl>-4-piperidinyl>-1H-indole hydrochloride

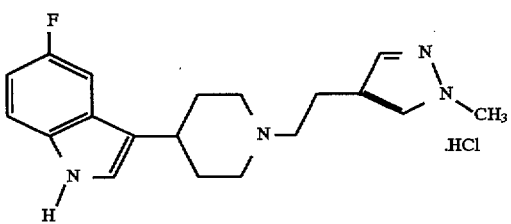

The preparation of Compound II, an important embodiment of the present invention, is described in Example 2 supra.

Compound III
5-hydroxy-3-(4-piperidinyl)-1H-indole oxalate

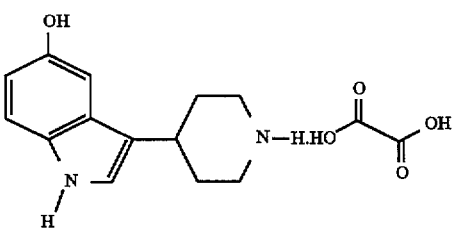

Compound III is available by the following procedure.
5-benzyloxy-3-[1,2,5,6-tetrahydro-4-pyridinyl]-1H-indole Starting with 5.0 gm (22 mMol) 5-benzyloxyindole and 6.88 gm (45 mMol) 4-piperidone.HCl H$_2$O, 6.53 gm (97.6%) of 5-benzyloxy-3-[1,2,5,6-tetrahydro-4-pyridinyl]-1H-indole were recovered as a light yellow solid by the procedure described in Preparation I. The material was used in the subsequent step without further purification.

Hydrogenation/Hydrogenolysis

To a solution of 1.23 gm (4 mMol) 5-benzyloxy-3-[1,2,5,6-tetrahydro-4-pyridinyl]-1H-indole in 50 mL 1:1 tetrahydrofuran:ethanol were added 0.3 gm 5% palladium on carbon and the reaction mixture hydrogenated at ambient temperature for 18 hours with an initial hydrogen pressure of 60 p.s.i. The reaction mixture was then filtered through a celite pad and the filtrate concentrated under reduced pressure. The residue was converted to the oxalate salt and 0.98 gm (80.0%) of Compound III were recovered as a brown foam.

m.p.=67° C.
MS(m/e): 216(M$^+$)
Calculated for C$_{13}$H$_{16}$N$_2$O.C$_2$H$_2$O$_4$: Theory: C, 58.81; H, 5.92; N, 9.14. Found: C, 58.70; H, 5.95; N, 9.39.

Compound IV
8-chloro-2-diethylamino-1,2,3,4-tetrahydronaphthalene hydrochloride

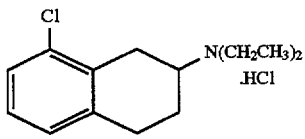

Compound IV is available by the following procedure.
8-chloro-2-tetralone

A mixture of 30.0 gm (0.176 mole) of o-chlorophenylacetic acid and 40.0 mL of thionyl chloride was stirred at ambient temperature for 18 hours. The volatiles were then removed in vacuo to give 32.76 gm (99.0%) of o-chlorophenylacetyl chloride as a transparent, pale yellow, mobile liquid.

NMR(CDCl$_3$): δ7.5–7.1 (m, 4H), 4.2 (s, 2H).

To a slurry of 46.5 gm (0.348 mole) AlC$_3$ in 400 mL dichloromethane at −78° C. was added a solution of 32.76 gm (0.174 mole) of the previously prepared o-chlorophenylacetyl chloride in 100 mL dichloromethane dropwise over 1 hour. The dry ice/acetone bath then was replaced with an ice/water bath and ethylene was bubbled into the reaction mixture during which time the temperature rose to 15° C. The ethylene addition was discontinued at the end of the exotherm and the reaction mixture was stirred at about 5° C. for 4 hours. Ice was then added to the reaction mixture to destroy aluminum complexes. Upon termination of the exotherm, the reaction mixture was diluted with 500 mL of water and stirred vigorously until all solids had dissolved. The phases were separated and the organic phase was washed with 3×400 mL 1N hydrochloric acid and 2×400 mL saturated aqueous sodium bicarbonate. The remaining organic phase was then dried over sodium sulfate and concentrated in vacuo to give a pale orange residue. The residue was dissolved in 1:1 hexane:diethyl ether and was poured over a flash silica column which was then eluted with 1:1 hexane:diethyl ether to give a light yellow residue which was crystallized from 4:1 hexane:diethyl ether to give 10.55 gm of the title compound.

NMR(CDCl$_3$): 7.5–7.2 (m, 3H), 3.7 (s, 2H), 3.3–3.0(t, J=7 Hz, 2H), 2.8–2.4 (t, J=7 Hz, 2H).

MS: 180(60), 165(9), 138(100), 117(52), 115(50), 103 (48), 89(20), 76(25), 74(18), 63(30), 57(9), 52(28), 51(20), 42(6), 39(32).

IR(nujol mull): 2950 cm$^{-1}$, 2927 cm$^{-1}$, 1708 cm$^{-1}$, 1464 cm$^{-1}$, 1450 cm$^{-1}$, 1169 cm$^{-1}$, 1141 cm$^{-1}$.

Reductive Amination

To a solution of 0.5 gm (2.78 mMol) 8-chloro-2-tetralone in 25 mL cyclohexane were added 1.4 mL (13.9 mMol) diethylamine followed by 0.1 gm p-toluenesulfonic acid monohydrate. The reaction mixture was then heated at reflux with constant water removal (Dean-Stark Trap) for 18 hours. The reaction mixture was then cooled to ambient and the volatiles removed under reduced pressure. The residue was then dissolved in 15 mL methanol to which were then added 1.5 mL acetic acid followed by the portionwise addition of 0.5 gm sodium borohydride. The reaction mixture was then stirred for 1 hour at ambient.

The reaction mixture was then diluted with 20 mL 10% HCl and stirred for an additional hour. The mixture was then extracted with diethyl ether and the remaining aqueous phase was poured over ice, made basic with ammonium hydroxide and extracted well with dichloromethane. These extracts were combined, dried over sodium sulfate and concentrated under reduced pressure. The residue was redissolved in dichloromethane and subjected to chromatography over basic alumina, eluting with dichloromethane. Fractions shown to contain product were combined and concentrated under reduced pressure. The residual oil was dissolved in diethyl ether and the solution saturated with hydrogen chloride. The viscous residue was crystallized from acetone/diethyl ether to give 0.20 gm (23.2%) of Compound IV as colorless crystals. m.p.=158°–159° C.

MS(m/e): 273
Calculated for C$_{14}$H$_{21}$NCl.HCl: Theory: C, 61.32; H, 7.72; N, 5.11. Found: C, 61.62; H, 7.94; N, 5.03.

Compound V
6-hydroxy-3-dimethylamino-1,2,3,4-tetrahydrocarbazole

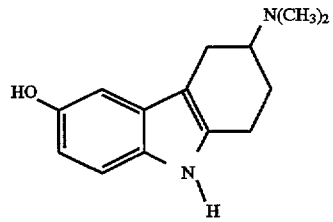

Compound V is available by the following procedure.
4-dimethylamino-1-cyclohexanone ethylene ketal To a solution of 5.0 gm (32 mMol) 1,4-cyclohexanedione mono-ethylene ketal and 10.80 gm (240 mMol) dimethylamine were added 2.0 mL acetic acid and the mixture was stirred at 0° C. for 1.5 hours. To this solution were then added 3.62 gm (58 mMol) sodium cyanoborohydride and the reaction stirred for an additional hour at ambient. The pH of the reaction mixture was adjusted to ~7 with 16 mL acetic acid and stirred 18 hours at ambient. The volatiles were removed under reduced pressure and the residue dissolved in cold 5% tartaric acid solution and then the aqueous phase was made basic with 5N sodium hydroxide. This aqueous phase was extracted well with dichloromethane. These organic extracts were combined and concentrated under reduced pressure to give 5.04 gm (85%) of the title compound as an oil.

4-dimethylamino-1-cyclohexanone 4.96 gm (26.8 mMol) 4-dimethylamino-1-cyclohexanone ethylene ketal were dissolved in 50 mL formic acid and the solution stirred at reflux for 18 hours. The reaction mixture was then cooled to ambient and the volatiles removed under reduced pressure to give 3.78 gm (100%) of the title compound.

6benzyloxy-3-dimethylamino-1,2,3,4-tetrahydrocarbazole

To a solution of 3.78 gm (26.8 mMol) 4-dimethylamino-1-cyclohexanone and 6.69 gm (26.8 mMol) 4-benzyloxyphenylhydrazine hydrochloride in 50 mL ethanol were added 2.17 mL (26.8 mMol) pyridine. To this solution were added 5×10 mL portions of water and the reaction mixture then stored at 0° C. for 18 hours. The reaction mixture was then diluted with an additional 50 mL of water and the mixture extracted well with dichloromethane. The combined organic extracts were dried over sodium sulfate and the volatiles removed under reduced pressure. The residual oil was subjected to flash silica gel chromatography, eluting with 9:1 chloroform:methanol. Fractions shown to contain the desired product were combined and concentrated under reduced pressure to give 2.14 gm (24.9%) of the title compound.

Hydrogenolysis

To a solution of 2.14 gm (6.7 mMol) 6-benzyloxy-3-dimethylamino-1,2,3,4-tetrahydrocarbazole in 50 mL ethanol were added 0.20 gm 10% palladium on carbon and the reaction mixture was hydrogenated at ambient temperature with an initial hydrogen pressure of 40 p.s.i. After 5 hours an additional charge of 0.20 gm 10% palladium on carbon were added and the reaction mixture repressurized with hydrogen to 40 p.s.i. for 4 hours. The reaction mixture was then filtered through a pad of celite and the filtrate concentrated under reduced pressure. The residue was subjected to Florisil chromatography, eluting with 9:1 chloroform:methanol. Fractions shown to contain the desired compound were combined and concentrated under reduced pressure. The residue was again subjected to Florisil chromatography, eluting with a gradient consisting of chloroform containing 2–10% methanol. Fractions shown to contain product were combined and concentrated under reduced pressure to give Compound V as a crystalline solid.

MS(m/e): 230(M$^+$)

Calculated for $C_{14}H_{18}N_2O$: Theory: C, 73.01; H, 7.88; N, 12.16. Found: C, 72.75; H, 7.83; N, 11.97.

Binding Assays

The binding affinities of compounds for various serotonin receptors were determined essentially as described above except that different cloned receptors are employed in place of the 5-HT$_{1F}$ receptor clone employed therein. The results of these binding experiments are summarized in Table II.

TABLE II

BINDING TO SEROTONIN (5-HT$_1$) RECEPTOR SUBTYPES (K$_i$ nM)

| Compound | 5-HT$_{1D\alpha}$ | 5-HT$_{1D\beta}$ | 5-HT$_{1B}$ | 5-HT$_{1F}$ |
|---|---|---|---|---|
| I | 4.8 | 9.6 | 2520.0 | 25.7 |
| II | 21.7 | 53.6 | 50.3 | 2.5 |
| III | 163.2 | 196.5 | 3.9 | 22.0 |
| IV | 13.5 | 145.3 | 813.0 | 129.2 |
| V | 791.0 | 1683.0 | 73.6 | 10.3 | cAMP Formation

All of the compounds of the panel were tested in the cAMP formation assay described supra and all were found to be agonists of the 5-HT$_{1F}$ receptor.

Protein Extravasation

Harlan Sprague-Dawley rats (225–325 g) or guinea pigs from Charles River Laboratories (225–325 g) were anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes were drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes (Rhodes Medical Systems, Inc.) were lowered through the holes in both hemispheres to a depth of 9 mm (rats) or 10.5 mm (guinea pigs) from dura.

The femoral vein was exposed and a dose of the test compound was injected intravenously (1 mL/kg) o Approximately 7 minutes later, a 50 mg/kg dose of Evans Blue, a fluorescent dye, was also injected intravenously. The Evans Blue complexed with proteins in the blood and functioned as a marker for protein extravasation. Exactly 10 minutes post-injection of the test compound, the left trigeminal ganglion was stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals were killed and exsanguinated with 20 mL of saline. The top of the skull was removed to facilitate the collection of the dural membranes. The membrane samples were removed from both hemispheres, rinsed with water, and spread flat on microscopic slides. Once dried, the tissues were coverslipped with a 70% glycerol/water solution.

A fluorescence microscope (Zeiss) equipped with a grating monochromator and a spectrophotometer was used to quantify the amount of Evans Blue dye in each sample. An excitation wavelength of approximately 535 nm was utilized and the emission intensity at 600 nm was determined. The microscope was equipped with a motorized stage and also interfaced with a personal computer. This facilitated the computer-controlled movement of the stage with fluorescence measurements at 25 points (500 μm steps) on each dural sample. The mean and standard deviation of the measurements was determined by the computer.

The extravasation induced by the electrical stimulation of the trigeminal ganglion was an ipsilateral effect (i.e. occurs only on the side of the dura in which the trigeminal ganglion was stimulated). This allows the other (unstimulated) half of the dura to be used as a control. The ratio of the amount of extravasation in the dura from the stimulated side compared to the unstimulated side dura was calculated. Saline controls yielded a ratio of approximately 2.0 in rats and 1.8 in guinea pigs. In contrast, a compound which effectively prevented the extravasation in the dura from the stimulated side would have a ratio of approximately 1.0. A dose-response curve was generated and the dose that inhibited the extravasation by 50% ($ID_{50}$) was approximated. This data is presented in Table III.

TABLE III

Inhibition of Protein Extravasation ($ID_{50}$ mMol/kg)

| Compound | i.v. $ID_{50}$ (mMol/kg) |
| --- | --- |
| I | $2.6 \times 10^{-8}$ |
| II | $8.6 \times 10^{-10}$ |
| III | $8.9 \times 10^{-9}$ |
| IV | $1.2 \times 10^{-7}$ |
| V | $8.7 \times 10^{-9}$ |

To determine the relationship of binding at various serotonin receptors to inhibition of neuronal protein extravasation, the binding affinity of all of the compounds to each of the $5\text{-}HT_{1D\alpha}$, $5\text{-}HT_{1D\beta}$, $5\text{-}HT_{1E}$ and $5\text{-}HT_{1F}$ receptors was plotted against their $ID_{50}$ in the protein extravasation model. A linear regression analysis was performed on each set of data and a correlation factor, $R^2$, calculated. The results of this analysis are summarized in Table IV.

TABLE IV

Correlation Factor ($R^2$) for Specific $5\text{-}HT_1$ Subtype Binding Affinity vs Inhibition of Protein Extravasation

| $5\text{-}HT_1$ Subtype | Correlation Factor ($R^2$) |
| --- | --- |
| $5\text{-}HT_{1D\alpha}$ | 0.20 |
| $5\text{-}HT_{1D\beta}$ | 0.03 |
| $5\text{-}HT_{1E}$ | 0.37 |
| $5\text{-}HT_{1F}$ | 0.96 |

An ideally linear relationship would generate a correlation factor of 1.0, indicating a cause and effect relationship between the two variables. The experimentally determined correlation factor between inhibition of neuronal protein extravasation and $5\text{-}HT_{1F}$ binding affinity is 0.96. This nearly ideal dependence of the $ID_{50}$ in the protein extravasation model on binding affinity to the $5\text{-}HT_{1F}$ receptor clearly demonstrates that the $5\text{-}HT_{1F}$ receptor mediates the inhibition of protein extravasation resulting from stimulation of the trigeminal ganglia.

While it is possible to administer a compound employed in the methods of this invention directly without any formulation, the compounds are usually administered in the form of Pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
|---|---|
| Compound of Example 23 | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Compound of Example 1 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Compound of Example 2 | 5 |
| Lactose | 95 |

The active mixture is mixed with lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Compound of Example 1 | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Compound of Example 3 | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Compound of Example 16 | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Compound of Example 49 | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
|---|---|
| Compound of Example 50 | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
|---|---|
| Compound of Example 53 | 250.0 mg |
| Isotonic saline | 1000 ml |

Formulation Example 10

A topical formulation may be prepared as follows:

| Ingredient | Quantity |
|---|---|
| Compound of Example 55 | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
|---|---|
| Compound of Example 47 | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:

1. A method for treating the pain of migraine and associated disorders which comprises administering to a mammal requiring such treatment a pharmaceutically effective amount of a compound of Formula I:

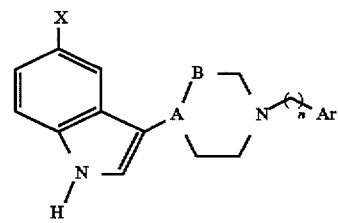

in which

A—B is —CH—$CH_2$— or —C=CH—;

X is H, halo, $C_1$–$C_4$ alkyl, $C_1$–$C_4$ alkoxy, $C_1$–$C_4$alkylthio, benzyloxy, hydroxy or carboxamido;

n is 1–4;

Ar is pyridinyl, pyrrolyl or a structure of Formula II:

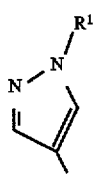

where $R^1$ is H, $C_1$–$C_6$ alkyl, $C_3$–$C_7$ cycloalkyl, $C_3$–$C_7$ cycloalkylmethyl, benzyl, phenyl or substituted phenyl and pharmaceutically acceptable acid addition salts thereof.

2. A method of claim 1, in which the compound is 5-fluoro-3-<1-<2-<1-methyl-1H-pyrazol-4-yl>ethyl>-4-piperidinyl>-1H-indole or a pharmaceutically acceptable salt or hydrate thereof.

3. A method of claim 1, in which the compound is 5-chloro-3-<1-<2-<1-methyl-1H-pyrazol-4-yl>ethyl>-4-piperidinyl>-1H-indole or a pharmaceutically acceptable salt or hydrate thereof.

4. A method of claim 1, in which the compound is 3-<1-<2-<1-propyl-1H-pyrazol-4-yl>ethyl>-4-piperidinyl>-1H-indole or a pharmaceutically acceptable salt or hydrate thereof.

5. A method of claim 1, in which the compound is 5-hydroxy-3-<1-<2-<1-propyl-1H-pyrazol-4-yl>ethyl>-4-piperidinyl>-1H-indole or a pharmaceutically acceptable salt or hydrate thereof.

6. A method of claim 1, in which the compound is 5-chloro-3-<1-<3-<1H-pyrazol-4-yl>propyl>-4-piperidinyl>-1H-indole or a pharmaceutically acceptable salt or hydrate thereof.

7. A method of claim 1, in which the compound is 5-chloro-3-<1,2,3,6-tetrahydro-1-<2-<1-(1-methylethyl)-1H-pyrazol-4-yl>ethyl>-4-pyridinyl>-1H-indole or a pharmaceutically acceptable salt or hydrate thereof.

8. A method of claim 1, in which the compound is 5-fluoro-3-<1-<2-<pyridin-3-yl>ethyl>-4-piperidinyl>-1H-indole or a pharmaceutically acceptable salt or hydrate thereof.

9. A method of claim 1, in which the compound is 5-hydroxy-3-<1-<2-<1-(1-methylethyl)-1H-pyrazol-4-yl>ethyl>-4-piperidinyl>-1H-indole or a pharmaceutically acceptable salt or hydrate thereof.

10. A method for the inhibition of neuronal protein extravasation comprising administering to a mammal in need thereof an effective amount of a compound of Formula I:

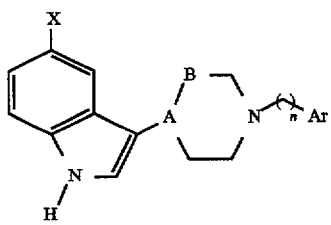

in which

A—B is —CH—CH$_2$— or —C=CH—;

X is H, halo, $C_1$–$C_4$ alkyl, $C_1$–$C_4$ alkoxy, $C_1$–$C_4$ alkylthio, benzyloxy, hydroxy or carboxamido;

n is 1–4;

Ar is pyridinyl, pyrrolyl or a structure of Formula II:

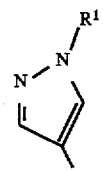

where $R^1$ is H, $C_1$–$C_6$ alkyl, $C_3$–$C_7$ cycloalkyl, $C_3$–$C_7$ cycloalkylmethyl, benzyl, phenyl or substituted phenyl or a pharmaceutically acceptable acid addition salt or hydrate thereof.

11. A method for the activation of 5-HT$_{1F}$ receptors in mammals comprising administering to a mammal in need of such activation an effective amount of a compound of Formula I:

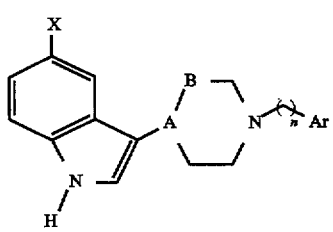

in which

A—B is —CH—CH$_2$— or —C=CH—;

X is H, halo, $C_1$–$C_4$ alkyl, $C_1$–$C_4$ alkoxy, $C_1$–$C_4$ alkylthio, benzyloxy, hydroxy or carboxamido;

n is 1–4;

Ar is pyridinyl, pyrrolyl or a structure of Formula II:

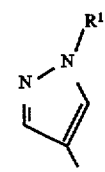

where $R^1$ is H, $C_1$–$C_6$ alkyl, $C_3$–$C_7$ cycloalkyl, $C_3$–$C_7$ cycloalkylmethyl, benzyl, phenyl or substituted phenyl or a pharmaceutically acceptable acid addition salt or hydrate thereof.

* * * * *